US008973162B1

(12) United States Patent
Bretan et al.

(10) Patent No.: US 8,973,162 B1
(45) Date of Patent: Mar. 10, 2015

(54) ASSISTIVE AND PROTECTIVE GARMENTS

(71) Applicants: Joel H. Bretan, Scottsdale, AZ (US); Vincent D. Del Vecchio, Scottsdale, AZ (US)

(72) Inventors: Joel H. Bretan, Scottsdale, AZ (US); Vincent D. Del Vecchio, Scottsdale, AZ (US)

( * ) Notice: Subject to any disclaimer, the term of this patent is extended or adjusted under 35 U.S.C. 154(b) by 0 days.

(21) Appl. No.: 13/624,901

(22) Filed: Sep. 22, 2012

Related U.S. Application Data

(60) Provisional application No. 61/538,702, filed on Sep. 23, 2011.

(51) Int. Cl.
*A41D 27/00* (2006.01)
*A41D 31/02* (2006.01)
*A63B 71/12* (2006.01)

(52) U.S. Cl.
USPC ............ 2/22; 2/239; 602/23; 602/27

(58) Field of Classification Search
CPC .... A63B 71/08; A63B 71/12; A63B 71/1225; A61F 5/0102; A41D 13/05; A41D 13/0543; A41D 13/06; A41D 13/065; A41D 13/00; A41D 2400/80; A41D 2400/82; A41D 2600/10
USPC ............ 602/75, 26, 23, 63, 27, 61, 6, 65, 76, 602/78; 2/22, 240, 160, 239, 309, 59, 61, 2/62, 911
See application file for complete search history.

(56) References Cited

U.S. PATENT DOCUMENTS

| | | | | |
|---|---|---|---|---|
| 3,856,008 A * | 12/1974 | Fowler et al. | | 602/62 |
| 3,983,870 A * | 10/1976 | Herbert et al. | | 602/63 |
| 4,084,586 A * | 4/1978 | Hettick | | 602/60 |
| 4,974,343 A * | 12/1990 | Davidson | | 36/89 |
| 5,010,597 A * | 4/1991 | Glover | | 2/242 |
| 5,154,690 A * | 10/1992 | Shiono | | 602/5 |
| 5,640,714 A * | 6/1997 | Tanaka | | 2/22 |
| 5,925,010 A * | 7/1999 | Caprio, Jr. | | 602/62 |
| 6,776,769 B2 * | 8/2004 | Smith | | 602/61 |
| 6,779,200 B1 * | 8/2004 | Shah | | 2/242 |
| 7,496,973 B2 * | 3/2009 | Jewell et al. | | 2/227 |
| 7,615,020 B2 * | 11/2009 | Nordt et al. | | 602/5 |
| 7,615,022 B2 * | 11/2009 | Nordt et al. | | 602/5 |
| 7,637,884 B2 * | 12/2009 | Nordt et al. | | 602/60 |
| 7,670,306 B2 * | 3/2010 | Nordt et al. | | 602/5 |
| 7,691,074 B2 * | 4/2010 | Nordt et al. | | 602/16 |
| 2002/0115950 A1 * | 8/2002 | Domanski et al. | | 602/23 |
| 2002/0123711 A1 * | 9/2002 | Smith | | 602/61 |
| 2004/0019950 A1 * | 2/2004 | Rast | | 2/77 |
| 2004/0054306 A1 * | 3/2004 | Roth et al. | | 601/152 |
| 2004/0193086 A1 * | 9/2004 | Cofre | | 602/20 |
| 2005/0027228 A1 * | 2/2005 | Binder et al. | | 602/41 |

(Continued)

*Primary Examiner* — Bobby Muromoto, Jr.
(74) *Attorney, Agent, or Firm* — Michael W. Goltry; Robert A. Parsons; Parsons & Goltry

(57) ABSTRACT

A garment consists of a close-fitting sleeve body formed of a stretch textile, and which includes an open upper end, an open lower end, and a body-receiving volume extending through the sleeve body from the open upper end to the open lower end. Opposed, spaced-apart, surface-gripping parts are applied exteriorly to the sleeve body near the open upper end and the open lower end, respectively. The surface-gripping parts are each formed of a gripping material different from the stretch textile, and the gripping material is slightly sticky or adhesive so as to cause the surface-gripping parts to grip, and to resist slipping relative to, surfaces they come in direct contact with without leaving a resulting residue on touched surfaces.

1 Claim, 9 Drawing Sheets

(56) References Cited

U.S. PATENT DOCUMENTS

| | | | |
|---|---|---|---|
| 2005/0132463 A1* | 6/2005 | Kathumbi-Jackson et al. | 2/51 |
| 2005/0132465 A1* | 6/2005 | Kathumbi-Jackson et al. | 2/114 |
| 2005/0204451 A1* | 9/2005 | Plut et al. | 2/161.6 |
| 2005/0209545 A1* | 9/2005 | Farrow et al. | 602/75 |
| 2006/0000478 A1* | 1/2006 | Taylor | 128/869 |
| 2006/0030805 A1* | 2/2006 | Nordt et al. | 602/26 |
| 2006/0030806 A1* | 2/2006 | Nordt et al. | 602/26 |
| 2006/0075538 A1* | 4/2006 | Anderson et al. | 2/69 |
| 2006/0075539 A1* | 4/2006 | Anderson et al. | 2/108 |
| 2006/0085894 A1* | 4/2006 | Yakopson et al. | 2/239 |
| 2006/0101554 A1* | 5/2006 | St-Germain | 2/123 |
| 2006/0137071 A1* | 6/2006 | Rampersad | 2/24 |
| 2006/0143767 A1* | 7/2006 | Yang et al. | 2/16 |
| 2006/0149180 A1* | 7/2006 | Phelen | 602/20 |
| 2006/0276735 A1* | 12/2006 | Phelen et al. | 602/21 |
| 2007/0106354 A1* | 5/2007 | Carstens | 607/112 |
| 2007/0192928 A1* | 8/2007 | Hanna | 2/159 |
| 2007/0197944 A1* | 8/2007 | Bruce et al. | 602/23 |
| 2007/0276310 A1* | 11/2007 | Lipshaw et al. | 602/62 |
| 2008/0109944 A1* | 5/2008 | Beebe et al. | 2/309 |
| 2008/0115248 A1* | 5/2008 | Meadows | 2/22 |
| 2008/0245361 A1* | 10/2008 | Brown | 128/118.1 |
| 2008/0249440 A1* | 10/2008 | Avitable et al. | 601/151 |
| 2008/0249441 A1* | 10/2008 | Avitable et al. | 601/151 |
| 2008/0249442 A1* | 10/2008 | Brown et al. | 601/152 |
| 2008/0249443 A1* | 10/2008 | Avitable et al. | 601/152 |
| 2008/0249444 A1* | 10/2008 | Avitable et al. | 601/152 |
| 2008/0249447 A1* | 10/2008 | Brown et al. | 602/13 |
| 2008/0249449 A1* | 10/2008 | Brown et al. | 602/20 |
| 2008/0249455 A1* | 10/2008 | Brown et al. | 602/75 |
| 2008/0249559 A1* | 10/2008 | Brown et al. | 606/202 |
| 2009/0070917 A1* | 3/2009 | Shoemaker | 2/161.1 |
| 2009/0137938 A1* | 5/2009 | Parivash | 602/63 |
| 2009/0255027 A1* | 10/2009 | Laitmon | 2/22 |
| 2009/0293173 A1* | 12/2009 | Gudzak | 2/160 |
| 2010/0056973 A1* | 3/2010 | Farrow et al. | 602/63 |
| 2010/0107297 A1* | 5/2010 | Brodbeck | 2/67 |
| 2010/0281593 A1* | 11/2010 | Aloy Font | 2/22 |
| 2010/0312160 A1* | 12/2010 | Creighton et al. | 602/62 |
| 2012/0065664 A1* | 3/2012 | Avitable et al. | 606/201 |
| 2012/0084899 A1* | 4/2012 | Yanagisawa et al. | 2/69 |
| 2012/0128883 A1* | 5/2012 | Avitable | 427/256 |
| 2012/0136290 A1* | 5/2012 | Avitable | 601/151 |
| 2012/0144544 A1* | 6/2012 | Telfer et al. | 2/20 |
| 2012/0159692 A1* | 6/2012 | Rees-Jones et al. | 2/69 |
| 2013/0053750 A1* | 2/2013 | Taylor | 602/75 |
| 2013/0172156 A1* | 7/2013 | Inzer | 482/93 |
| 2013/0204172 A1* | 8/2013 | Viehweg et al. | 602/26 |
| 2013/0212767 A1* | 8/2013 | Nordstom et al. | 2/69 |

* cited by examiner

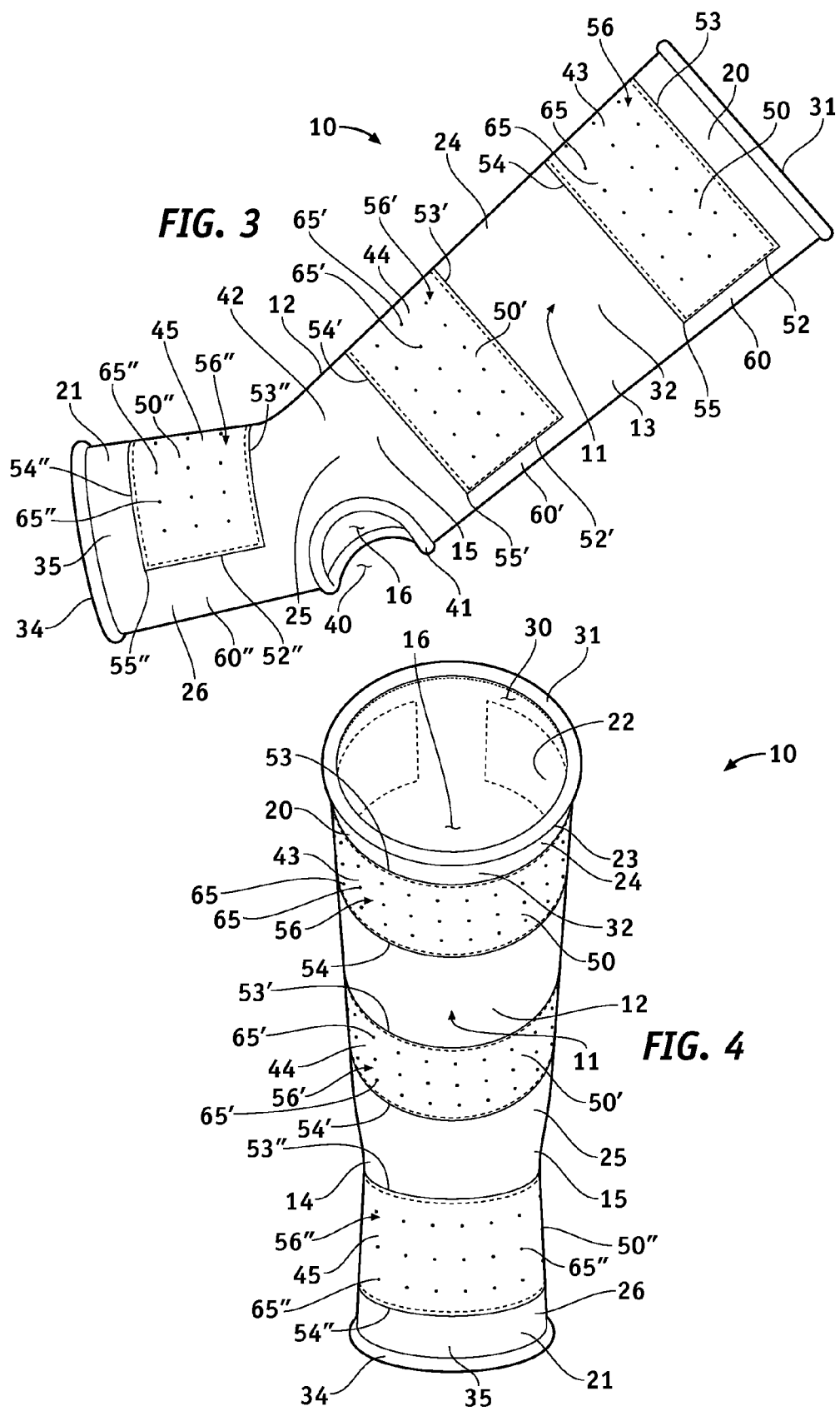

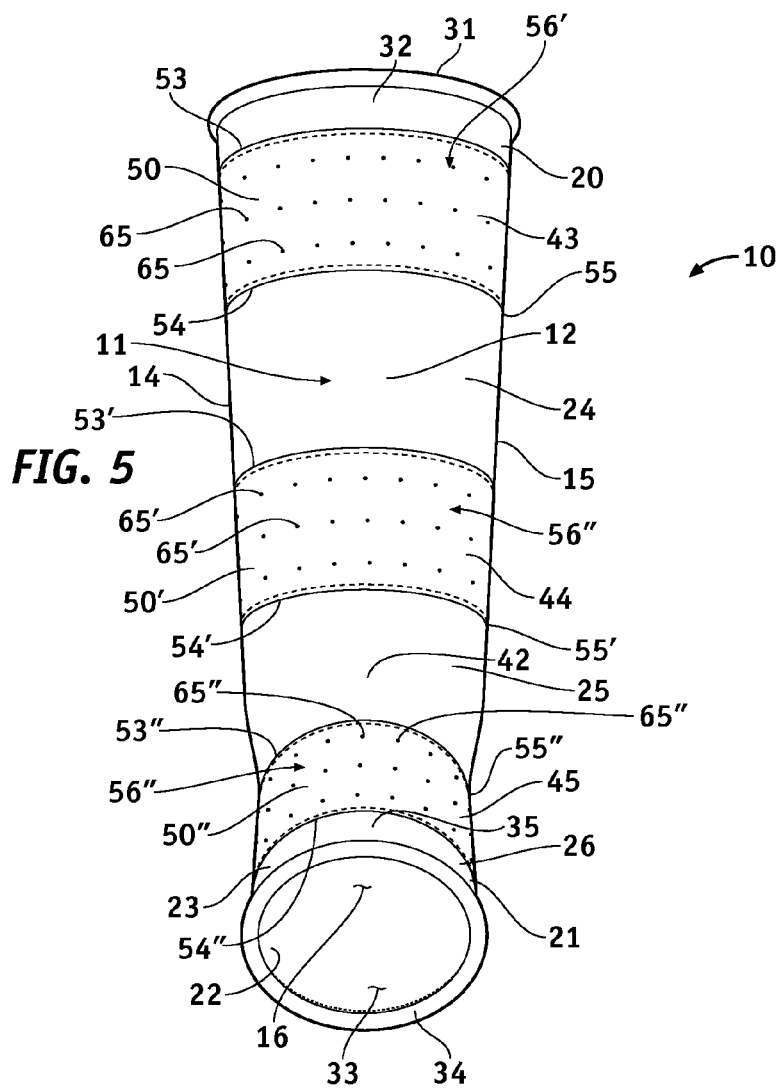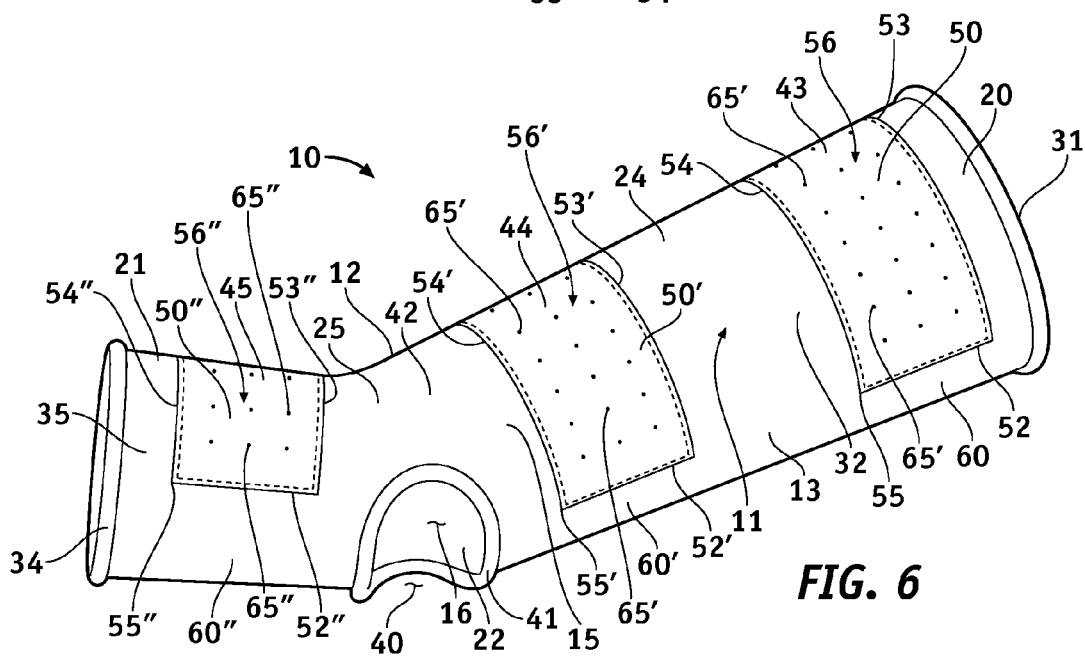

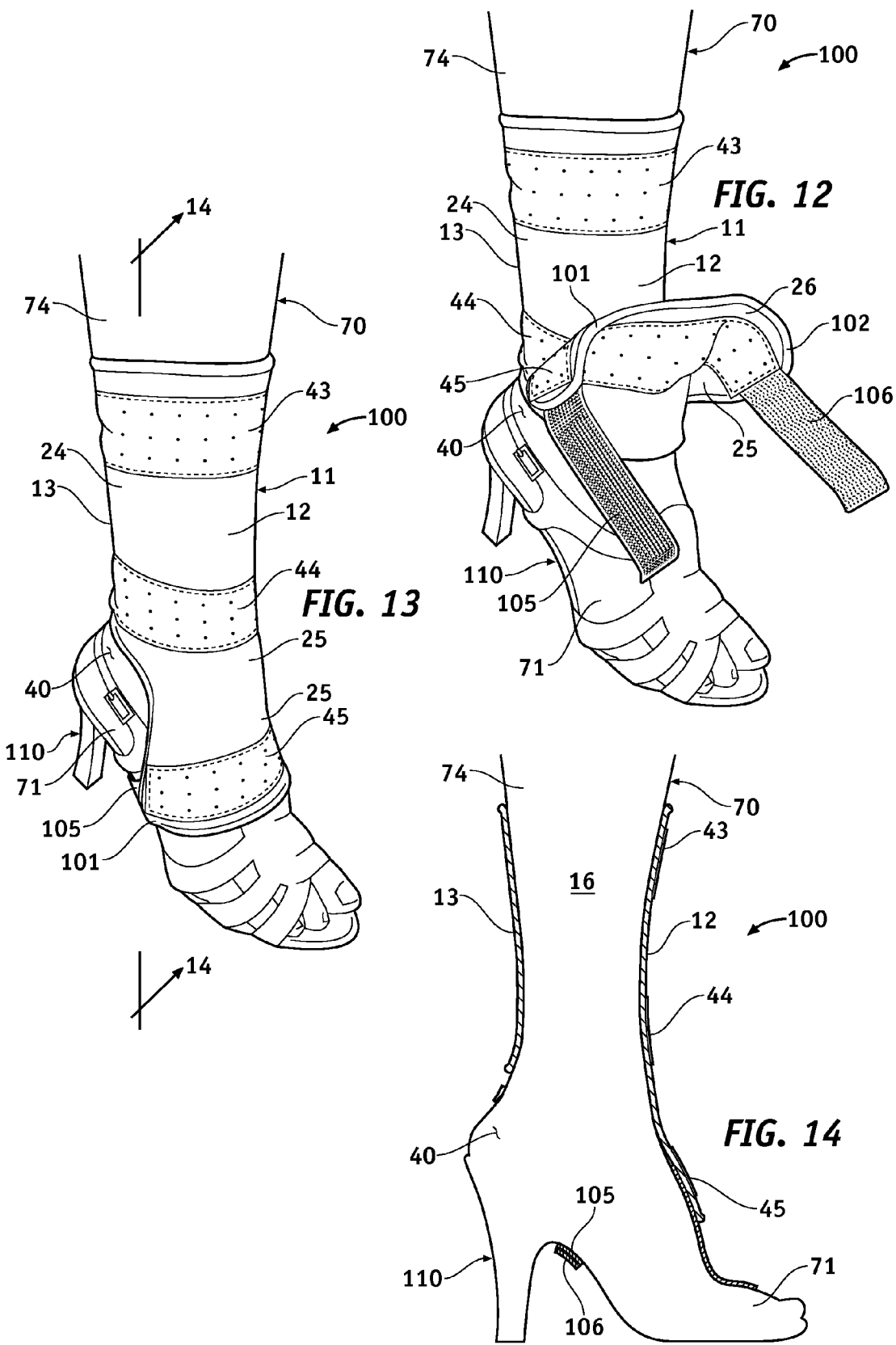

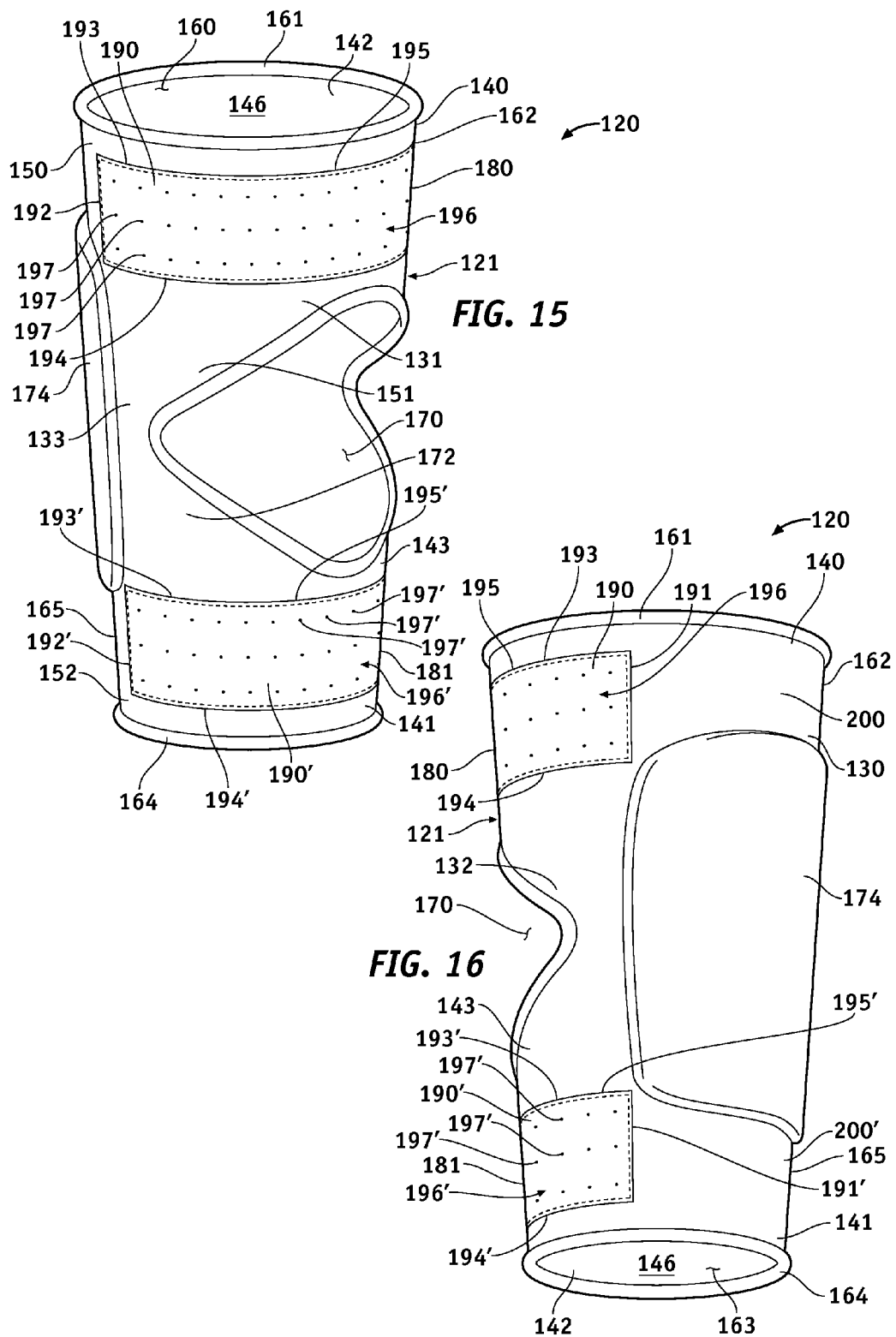

ASSISTIVE AND PROTECTIVE GARMENTS

FIELD OF THE INVENTION

The present invention relates generally to garments and, more particularly, to a specialized assistive and protective garment for use in exercising, sports, gymnastics, and pole dance activities.

BACKGROUND OF THE INVENTION

Pole dance is a performance art involving moving, dancing, and interacting with a metal pole. It is a competitive sport in which pole-dancing performers dance around and upon a pole. Performers climb the pole, hold and extend themselves outwardly at various angles from the pole, invert themselves while gripping the pole, and spin around the pole, often while maintaining one of the above poses. Pole-dancing requires significant knowledge, strength, flexibility, endurance, and training to become proficient.

The pole used during a pole-dancing activity is typically approximately two inches in diameter and eight or more feet high and is mounted to the ground or between the ground and an upper support. Poles are generally made of a strong, rigid material such as metal, especially steel, aluminum, brass, and the like. The outer surface of the pole is generally smooth and slick, as is typical of a metal surface.

Performers dancing with a pole necessarily touch the pole with their feet and legs. A performer may use his or her legs and feet to touch the pole, grip the pole, depend from the pole, cantilever out from the pole, "stand" on the pole, "sit" on the pole, spin about the pole, and interact in other ways with the pole. The skin of the performer's legs and feet is thus placed in frequent contact with the pole while gripping, hanging, spinning, and performing other moves from the pole, causing the skin and tissue to become bruised, burned, and rubbed with prolonged training.

Accordingly what is needed is a protective and assistive garment useful in assisting and protecting a user during pole dance activities and also other selected activities, such as sports activities, gymnastics, exercising activities, and the like, where a user may come into contact with sports, gymnastics, and exercising equipment or implements.

SUMMARY OF THE INVENTION

According to the principle of the invention, an assistive and protective garment for use in exercising, sports, gymnastics, and pole dance activities includes an assistive and protective garment consisting of a sleeve body having a front portion and an opposing rear portion, opposed side portions, an upper end which is open, and an opposing lower end which is open. The sleeve body includes an outer surface and opposing inner surface bounding a volume to receive a human appendage, such as a lower leg, ankle, and foot of a human lower appendage in one embodiment, or a lower thigh, knee, and upper leg of human lower appendage in another embodiment. The outer surface of the sleeve body carries separate, spaced-apart, gripping parts for gripping onto or otherwise grippingly engaging a metal surface, such as the metal surface of a pole dance pole, or other surface.

A garment constructed and arranged in accordance with the principle of the invention includes a close-fitting sleeve body formed of a stretch textile and which includes an open upper end, an open lower end, and a body-receiving volume extending through the sleeve body from the open upper end to the open lower end. Opposed, separate, spaced-apart, surface-gripping parts are applied exteriorly to the sleeve body near the open upper end and the open lower end, respectively. The surface-gripping parts are each formed of a gripping material different from the stretch textile, the gripping material being slightly sticky or adhesive so as to cause the surface-gripping parts to grip, and to resist slipping relative to, surfaces they come in direct contact with without leaving a resulting residue on touched surfaces. In a preferred embodiment, the stretch textile is a 2-way stretch textile that resists lengthwise stretching in a longitudinal direction from the open upper end to the open lower end, and that elastically stretches and constricts radially in a crosswise direction perpendicular to the longitudinal direction allowing the close-fitting sleeve body to elastically circumferentially expand and contract. The close-fitting sleeve body defines a plurality of body-receiving parts. In one embodiment, the plurality of body-receiving parts includes a leg-receiving part and an opposed foot-receiving part formed on either side of an ankle-receiving part, wherein the leg-receiving part extends from the open upper end to the ankle-receiving part, the foot-receiving part extends from the open lower end to the ankle-receiving part, and wherein one of the surface gripping parts is carried by the leg-receiving part, and the other one of the surface-gripping parts is carried by the foot-receiving part. In another embodiment, the plurality of body-receiving parts includes a thigh-receiving part and an opposed leg-receiving part formed on either side of a knee-receiving part, wherein the thigh-receiving part extends from the open upper end to the knee-receiving part, and the leg-receiving part extends from the open lower end to the knee-receiving part, and wherein one of the surface gripping parts is carried by the thigh-receiving part, and the other one of the surface-gripping parts is carried by the thigh-receiving part. In a further embodiment, a knee pad is formed in the knee-receiving part.

Consistent with the foregoing summary of the invention and the ensuing descriptions, all of which are to be taken together, the invention contemplates associated garment embodiments.

BRIEF DESCRIPTION OF THE DRAWINGS

Referring to the drawings:

FIGS. 1, 2, and 3 are perspective views of an assistive and protective garment constructed and arranged in accordance with the principle of the invention;

FIG. 4 is top front perspective view of the embodiment of FIG. 1;

FIG. 5 is a bottom front perspective view of the embodiment of FIG. 1;

FIG. 6 is a perspective view somewhat similar to that of FIG. 3;

FIG. 12 is a perspective view of the embodiment of FIG. 10 shown as it would appear partially installed on a shoe-wearing lower extremity of a performer;

FIG. 13 is a view similar to that of FIG. 12 showing the garment as it would appear being installed and worn on the shoe-wearing lower extremity of the performer;

FIG. 14 is a section view taken along line 14-14 of FIG. 13;

FIG. 15 is a rear perspective view of yet another alternate embodiment of an assistive and protective garment constructed and arranged in accordance with the principle of the invention;

FIG. 16 is a front perspective view of the embodiment of FIG. 15; and

DETAILED DESCRIPTION

Figures 1, 2:
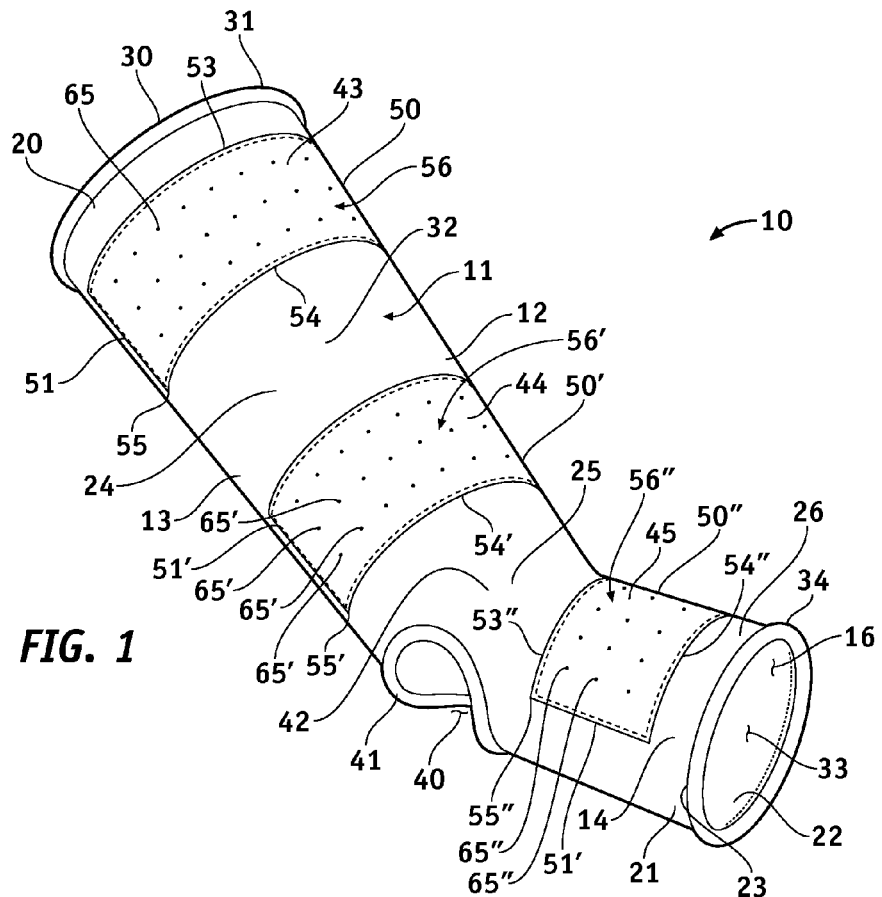

In general, a garment constructed and arranged in accordance with the principle of the invention includes a close-fitting sleeve body formed of a stretch textile and which includes an open upper end, an open lower end, and a body-receiving volume extending through the sleeve body from the open upper end to the open lower end. Opposed, separate, spaced-apart, surface-gripping parts are applied exteriorly to the sleeve body near the open upper end and the open lower end, respectively. The surface-gripping parts are each formed of a gripping material different from the stretch textile, the gripping material being slightly sticky or adhesive so as to cause the surface-gripping parts to grip, and to resist slipping relative to, surfaces they come in direct contact with without leaving a resulting residue on touched surfaces. In a preferred embodiment, the stretch textile is a 2-way stretch textile that resists lengthwise stretching in a longitudinal direction from the open upper end to the open lower end, and that elastically stretches and constricts radially in a crosswise direction perpendicular to the longitudinal direction allowing the close-fitting sleeve body to elastically circumferentially expand and contract. The close-fitting sleeve body defines a plurality of body-receiving parts. In one embodiment, the plurality of body-receiving parts includes a leg-receiving part and an opposed foot-receiving part formed on either side of an ankle-receiving part, wherein the leg-receiving part extends from the open upper end to the ankle-receiving part, the foot-receiving part extends from the open lower end to the ankle-receiving part, and wherein one of the surface gripping parts is carried by the leg-receiving part, and the other one of the surface-gripping parts is carried by the foot-receiving part. In another embodiment, the plurality of body-receiving parts includes a thigh-receiving part and an opposed leg-receiving part formed on either side of a knee-receiving part, wherein the thigh-receiving part extends from the open upper end to the knee-receiving part, and the leg-receiving part extends from the open lower end to the knee-receiving part, and wherein one of the surface gripping parts is carried by the thigh-receiving part, and the other one of the surface-gripping parts is carried by the thigh-receiving part. In a further embodiment, a knee pad is formed in the knee-receiving part.

Turning now to the drawings, in which like reference characters indicate corresponding elements throughout the several views, attention is directed in relevant part to FIGS. 1-8 illustrating an assistive and protective garment 10 for use in exercising, sports, gymnastics, pole dance activities, and the like. Garment 10 is a close-fitting garment in the form of a sleeve or sleeve body, and is a body covering body portions including the foot and ankle and reaching to between the ankle and knee of the leg of a performer. The term "close-fitting" according to this disclosure means fitting closely but comfortably, a close fit. Sleeve body 11 is a tube or tubular garment that includes a front or front portion 12 and an opposing rear or rear portion 13, opposed sides or side portions 14 and 15, an upper end 20, which is open to admit a body part therethrough, and an opposing lower end 21, which is also open to admit a body part therethrough. Opposed front and rear portions 12 and 13 and opposed side portions 14 and 15 extend along the entire length of sleeve body 11 from upper end 20 of sleeve body 11 to lower end 21 of sleeve body 11. Side 14 is the right side of sleeve body 11, and side 15 is the left side of sleeve body 11. Sleeve body 11 further includes opposed inner and outer surfaces 22 and 23 that extend along the entire length of sleeve body 11 from upper end 20 to lower end 21. Front and rear portions 12 and 13, and side portions 14 and 15 of the sleeve body 11 tube or tubular garment are formed integrally with each other and define the inner and outer surfaces 22 and 23 of sleeve body 11, all of which extend from upper end 20 of sleeve body 11 to lower end 21 of sleeve body 11. Inner surface 22 of sleeve body 11 bounds or otherwise defines volume 16 through sleeve body 11 from upper end 20 to lower end 21 to receive therein a lower leg, ankle, and foot of the lower appendage of a human performer. Volume 16 is a body-receiving volume that extends through sleeve body 11 from upper end 20, which is open, to lower end 21, which is also open. When installed onto a body appendage, such as the lower leg, ankle, and foot of the lower appendage of a human performer, the applied body appendage is applied to volume 16 and front portion 12 is applied to and across the top or front side of the performer's foot, ankle, and lower leg between the ankle and the knee, rear portion 13 is applied to and across the bottom or backside of the performer's foot, ankle, and lower leg between the ankle and the knee, and side portions 14 and 15 are applied to and across the opposed sides, respectively, of the performer's foot, ankle, and lower leg between the ankle and the knee.

Sleeve body 11 includes/defines body-receiving parts or portions including a leg-receiving part or portion, a foot-receiving part or portion, and an ankle-receiving part or portion between the leg-receiving part or portion and the foot-receiving part or portion. The leg-receiving part or portion is a sleeve, sleeve segment, or sleeve part 24 of sleeve body 11, the foot-receiving part or portion is a sleeve, sleeve segment, or sleeve part 26 of sleeve body 11, and the ankle-receiving part or portion is a sleeve, sleeve segment, or sleeve part 25 of sleeve body 11 located between sleeves 24 and 26 at an intermediate location of sleeve body 11 between upper and lower ends 20 and 21. Sleeves 24, 25, and 26 are similar in structure and are segments or parts of the entire sleeve that makes up sleeve body 11. Sleeves 24, 25, and 26 are integrally formed with each other so as to cooperate to form sleeve body 11. In this regard, sleeve body 11 is considered a major sleeve, and sleeves 24,25,26 defining the leg-, ankle-, and foot-receiving parts are considered minor sleeves of sleeve body 11.

Leg-receiving sleeve 24 receives and accommodates a portion of the leg of a human performer between the knee and the ankle and has a leg opening or mouth 30 at upper end 20 of sleeve body 11 that defines the open characteristic of upper end 20. Leg-receiving sleeve 24 extends from mouth 30 to ankle-receiving sleeve 25. Mouth 30 is defined by a lip 31 formed in upper end 20 of sleeve body 11. Lip 31 encircles and defines mouth 30, which leads to or otherwise into volume 16 bound by sleeve body 11 at upper end 20 of sleeve body 11. Lip 31 is an annular band formed of conventional elastic band material having deformable, elastic, and size- and shape-memory material characteristics, which cause lip 31 to tend to elastically constrict inwardly in a radial direction against a lower leg that has been applied to leg-receiving sleeve 24. As the term is used herein, "radial" means generally directed along a line extending inwardly and outwardly relative to a center of volume 16 bound by sleeve body 11 and through sleeve body 11. Leg-receiving sleeve 24 of sleeve body 11 is characterized in that it is a continuous sidewall 32 that extends between mouth 30 and ankle-receiving sleeve 25. According to this disclosure, the term "girdle" is used throughout this disclosure and means to closely encircle or fit around and embrace and support a body part, or otherwise something that closely encircles or fits around and embraces and supports a body part. Sidewall 32 of sleeve body 11 encircles volume 16 between upper end 20 and ankle-receiving sleeve 25 and girdles a performer's lower leg applied to volume 16, which means that that sidewall 32 of leg-receiving sleeve 24 of sleeve body 11 closely encircles or fits around and embraces and supports the lower leg within leg-receiving sleeve 24.

Foot-receiving part or sleeve 26 receives and accommodates a foot of the lower appendage of a human performer, and has a toe mouth or opening 33 at lower end 21 of sleeve body 11 that defines the open characteristic of lower end 21 of sleeve body 11. Foot-receiving sleeve 26 extends from toe opening 33 to ankle-receiving sleeve 25. Toe opening 33 is defined by a lip 34 formed in lower end 21 of sleeve body 11. Lip 34 encircles and defines toe opening 33, which leads to or otherwise into volume 16 bound by sleeve body 11 at lower end 21 of sleeve body 11. Lip 34 is an annular band formed of conventional elastic band material having deformable, elastic, and size- and shape-memory material characteristics, which cause lip 34 to tend to elastically constrict inwardly in a radial direction against a foot that has been applied to foot-receiving sleeve 26. Foot-receiving sleeve 26 is characterized in that it is a continuous sidewall 35 that extends between toe opening 33 and ankle-receiving sleeve 25. Sidewall 35 encircles volume 16 between lower end 21 and ankle-receiving sleeve 25 and girdles a portion of a foot applied to volume 16, namely, the instep region of the foot between the toes and the ankle.

Ankle-receiving sleeve 25 accommodates an ankle and heel of the lower appendage of a human performer, and extends between leg-receiving sleeve 24 and foot-receiving sleeve 26. Ankle-receiving sleeve 25 is formed with a heel opening 40 located along and through rear portion 13 of sleeve body 11 at a generally intermediate location with respect to ankle-receiving sleeve 25 to receive therethrough a human heel leaving the human heel exposed and not confined. Heel opening 40 is defined by a lip 41. Lip 41 encircles and defines heel opening 40 and leads to or otherwise into volume 16 bound by sleeve body 11 at ankle-receiving sleeve 25 in a direction from rear portion 13. Lip 41 is an annular band formed of conventional elastic band material having deformable, elastic, and size- and shape-memory material characteristics, which cause lip 41 to tend to elastically constrict inwardly in a radial direction against a heel of an ankle that has been applied to ankle-receiving sleeve 25. Ankle-receiving sleeve 25 has an otherwise continuous sidewall 42 formed with heel opening 40 between leg-receiving sleeve 24 and foot-receiving sleeve 26. Sidewall 42 encircles volume 16 between leg-receiving sleeve 24 and foot-receiving sleeve 26 and girdles the ankle applied to volume 16 between leg-receiving sleeve 24 and foot-receiving sleeve 26.

Sleeve body 11 is constructed of a stretch fabric or textile, which is a fabric or textile having deformable, pliant, stretch or elastic, elastically constrictive, and size- and shape-memory material characteristics. Suitable stretch fabric or textile material include, for example, neoprene stretch fabric, spandex or elastane stretch fabric, polyester stretch fabric, or the like that stretches and that is stretchable to allow garment 10 to fit many different sizes of lower appendages and to hold garment 10 firmly in place against the appendage so as not to slip, twist, or ride up or down the appendage. In a preferred embodiment, sleeve body 11 is constructed from a 2-way stretch fabric/textile that is woven, knitted, or otherwise arranged in a common and well-known weave pattern so as to provide an elastically constrictive characteristic in one direction, characterized in that sleeve body 11 resists lengthwise stretching in a longitudinal direction from upper end 20 to lower end 21, and that elastically stretches and constricts radially in a crosswise direction perpendicular to the described longitudinal direction allowing sleeve body 11 to elastically circumferentially expand and contract to so as to accommodate many different sizes of legs, ankles, and feet. As the terms are used here, "longitudinal" means generally directed along a direction extending between upper and lower ends 20 and 21 of garment 10. Sleeve body 11 has a thickness in the radial direction which is compressible and which is increased along front portion 12 of ankle-receiving sleeve 25 and along front portion of 12 of foot-receiving sleeve 26 proximate to ankle-receiving sleeve 25. Outer surface 23 of sleeve body 11 is smooth so as to pass freely over surfaces such as metal.

In accordance with the principle of the invention, garment 10 is formed with and carries a plurality of gripping parts. These gripping parts are, more specifically, surface-gripping parts, which are located exteriorly and which are useful for gripping surfaces against which they are applied. And so when garment 10 is worn, the exterior gripping parts applied exteriorly to garment 10 may be applied against surfaces to assist a user in maneuvering upon and against such surfaces. In garment 10, the gripping parts or surface-gripping parts include three, separate gripping parts, including an upper gripping part 43, a lower gripping part 45, and an intermediate gripping part 44 located between the upper and lower gripping parts 43 and 45. Upper, intermediate, and lower gripping parts 43,44,45 are tack strips and are applied exteriorly to outer surface 23 of sleeve body 21 and are applied to and extend across front portion 12 so as to be available for gripping surfaces they come in contact with in a direction toward front portion 12 tending to cause gripping parts 43,44,45 to resist slipping across surfaces against which they are applied.

Upper gripping part 43 and intermediate gripping part 44 are spaced-apart and separate from one another and are carried by leg-receiving sleeve 24 between upper end 20 of sleeve body 11 and ankle-receiving sleeve 25, and lower gripping part 45 is spaced-apart and separate from upper gripping part 43 and intermediate gripping part 44 and is carried by foot-receiving sleeve 26. Upper gripping part 43 is located near upper end 20 of sleeve body 11, intermediate gripping part 44 is located near ankle-receiving sleeve 25 between upper gripping part 43 and ankle-receiving sleeve 45, including heel opening 40, and lower gripping part 45 is located near ankle-receiving sleeve 25 between lower end 21 and ankle-receiving sleeve 25, including heel opening 40. Upper gripping part 43, intermediate gripping part 44, and lower gripping part 45 are carried by sleeve body 11 and are considered a part of, or otherwise an extension of, sleeve body 11, but are made of a material that is different from the material of sleeve body 11 so as to provide the gripping function as disclosed herein, which is a function that the material of sleeve body 11 does not provide. Upper gripping part 43, intermediate gripping part 44, and lower gripping part 45 are substantially coextensive being substantially equal in size and in shape, and are each a flat, elongate tack strip of gripping material having the properties of flexibility, pliancy, deformability, inelasticity, and tackiness, which means that they are each slightly sticky or adhesive in nature that grip surfaces they come in contact with and resist slipping without leaving a resulting residue on touched objects. Preferably, upper, intermediate, and lower gripping parts 43,44,45 are fashioned of polyvinyl chloride (PVC) vinyl.

Upper gripping part 43 is circumferentially located upon and about outer surface 23 of sleeve body 11 near upper end 20 and extends across outer surface 23 of front portion 12 of sleeve body 11 from side portion 14 near rear portion 13 to side portion 15 near rear portion 13. Intermediate gripping part 44 located near ankle-receiving sleeve 25 between upper gripping part 43 and ankle-receiving sleeve 45 is, identically to that of upper gripping part 43, circumferentially located upon and about outer surface 23 of sleeve body 11 and extends across outer surface 23 of front portion 12 of sleeve body 11 from side portion 14 near rear portion 13 to side portion 15 near rear portion 13. Lower gripping part 45 located near ankle-receiving sleeve 25 between lower end 21 and ankle-receiving sleeve 25 is, identically to that of upper and intermediate gripping parts 43 and 44, circumferentially located upon and about sleeve body 11 near lower end 21 and extends across outer surface 23 of front portion 12 of sleeve body 11 from side portion 14 near rear portion 13 to side portion 15 near rear portion 13. Upper, intermediate, and lower gripping parts 43,44,45 extend across outer surface 23 of front portion 12 of sleeve body 11 as described in a transverse direction relative to the longitudinal direction of sleeve body 11 extending from upper end 20 to lower end 21 of sleeve body 11.

Upper gripping part 43 includes an inner surface (not shown) applied directly to outer surface 23 of sleeve body 11, and an opposing, exposed outer surface 50 for surface gripping. Upper gripping part 43 is formed with opposed, parallel side marginal edges 51 and 52, and opposed, parallel top and bottom marginal edges 53 and 54, which together cooperate to form a perimeter 55 bounding/encircling the inner surface (not shown) and the outer surface 50 of upper gripping part 43. In the embodiment shown in FIG. 1, upper gripping part 43 is affixed directly to outer surface 23 of sleeve body 11 by stitching applied along perimeter 55 between upper gripping part 43 and sleeve body 11. The stitching is preferably nylon stitching or the like that is strong, resilient, and resistant to tearing. In other embodiments, upper gripping part 43 is affixed to sleeve body 11 with glue, heat bonding, or the like.

Figure 7:
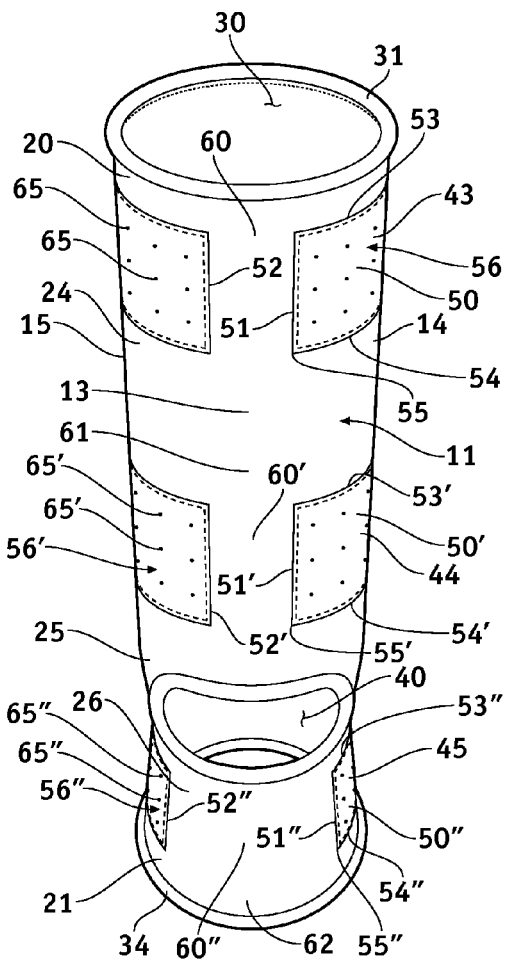
FIG. 7 is a top rear perspective view of the embodiment of FIG. 1.

Upper gripping part 43 is applied to, and extends across, leg-receiving sleeve 24 of sleeve body 11 at a contact area, which is denoted generally at 56. Contact area 56 is defined by outer surface 50 and extends between top and bottom marginal edges 52 and 54 of upper gripping part 43, and from side marginal edge 51 of upper gripping part 43 at side portion 14 of sleeve body 11 and along front portion 12 of sleeve body 11 to opposed side marginal edge 52 of upper gripping part 43 at side portion 15 of sleeve body 11. There is a gap 60 between opposed side marginal edges 51 and 52 of upper gripping part 43 exposing therebetween rear portion 13 of leg-receiving sleeve 24 of sleeve body 11 as shown in FIG. 7. Gap 60 is free of upper gripping part 43. Because upper gripping part 43 is formed of a gripping material that has the tacky/gripping material characteristic as described above, outer surface 50 of upper gripping part 43 is slightly sticky or adhesive so as to have a tacky/gripping property or otherwise a tacky/gripping material characteristic as is typical of PVC vinyl, that grippingly engages a surface, such as a metal surface, so that the touched surface resists slipping across upper gripping part 43 when in direct contact with upper gripping part 43, and yet upper gripping part 43 does not leave a sticky or adhesive residue on the surface it directly engages or touches. Upper gripping part 43 is formed with perforations 65 such that upper gripping part 43 is perforated to provide vapor transmission from sleeve body 11 through inner surface of upper gripping part 43 to outer surface 50.

With the exception of their respective locations on sleeve body 11, intermediate gripping part 44 and lower gripping part 45 are identical in every respect to upper gripping part 43, and the foregoing discussion of upper gripping part 43 applies equally to intermediate and lower gripping parts 44 and 45. For reference purposes, common reference characters used to describe the features of upper gripping part 43 are also used to denote the features of intermediate gripping part 44 and lower gripping part 45, and, for clarity, incorporate a prime ("'") for the features of intermediate gripping part 44, and a double-prime ("''") for the features of lower gripping part 45. In common with upper gripping part 43, intermediate gripping part 44 is circumferentially located about sleeve body 11 and shares an inner surface (not shown), outer surface 50', opposed side marginal edges 51' and 52', opposed top and bottom marginal edges 53' and 54', perimeter 55' bounding outer surface 50', the defined contact area 56', and gap 60' exposing rear portion 13 of sleeve body 11 between opposed side marginal edges 51' and 52', and also perforations 65'. Intermediate gripping part 44 includes an inner surface (not shown) applied directly to outer surface 23 of sleeve body 11, and opposing, exposed outer surface 50' for surface gripping. Intermediate gripping part 44 is formed with opposed, parallel side marginal edges 51' and 52', and opposed, parallel top and bottom marginal edges 53' and 54', which together cooperate to form perimeter 55' bounding/encircling the inner surface (not shown) and the outer surface 50' of intermediate gripping part 44. Intermediate gripping part 44' is affixed directly to outer surface 23 of sleeve body 11 by stitching applied along perimeter 55' between intermediate gripping part 43' and sleeve body 11. The stitching is preferably nylon stitching or the like that is strong, resilient, and resistant to tearing. In other embodiments, intermediate gripping part 44 is affixed to sleeve body 11 with glue, heat bonding, or the like.

Intermediate gripping part 44 is applied to, and extends across, leg-receiving sleeve 24 of sleeve body 11 near ankle-receiving sleeve 25 between ankle-receiving sleeve 25 and upper gripping part 43 near upper end 20 at a contact area, which is denoted generally at 56'. Contact area 56' is defined by outer surface 50' and extends between top and bottom marginal edges 52' and 54' of intermediate gripping part 44, and from side marginal edge 51' of intermediate gripping part 44 at side portion 14 of sleeve body 11 and along front portion 12 of sleeve body 11 to opposed side marginal edge 52' of intermediate gripping part 44 at side portion 15 of sleeve body 11. There is a gap 60' between opposed side marginal edges 51' and 52' of intermediate gripping part 44 exposing therebetween rear portion 13 of leg-receiving sleeve 24 of sleeve body 11 near ankle-receiving sleeve 25 as shown in FIG. 7. Gap 60' is free of intermediate gripping part 44. Because intermediate gripping part 44 is formed of a gripping material that has the tacky/gripping material characteristic as described above, outer surface 50' of intermediate gripping part 44 is slightly sticky or adhesive so as to have a tacky/gripping property or otherwise a tacky/gripping material characteristic as is typical of PVC vinyl, that grippingly engages a surface, such as a metal surface, so that the touched surface resists slipping across intermediate gripping part 44 when in direct contact with intermediate gripping part 44, and yet intermediate gripping part 44 does not leave a sticky or adhesive residue on the surface it engages or touches. Intermediate gripping part 44 is formed with perforations 65' such that intermediate gripping part 44 is perforated to provide vapor transmission from sleeve body 11 through inner surface of intermediate gripping part 44 to outer surface 50.

In common with upper gripping part 43, lower gripping part 45 is circumferentially located about sleeve body 11 and shares an inner surface (not shown), outer surface 50", opposed side marginal edges 51" and 52", opposed top and bottom marginal edges 53" and 54", perimeter 55" bounding outer surface 50", the defined contact area 56", and gap 60" exposing rear portion 13 of sleeve body 11 between opposed side marginal edges 51" and 52", and also perforations 65". Lower gripping part 45 includes an inner surface (not shown) applied directly to outer surface 23 of sleeve body 11, and opposing, exposed outer surface 50" for surface gripping. Lower gripping part 45 is formed with opposed, parallel side marginal edges 51" and 52", and opposed, parallel top and bottom marginal edges 53" and 54", which together cooperate to form perimeter 55" bounding/encircling the inner surface (not shown) and the outer surface 50" of lower gripping part 45. Lower gripping part 45" is affixed directly to outer surface 23 of sleeve body 11 by stitching applied along perimeter 55" between intermediate gripping part 43" and sleeve body 11. The stitching is preferably nylon stitching or the like that is strong, resilient, and resistant to tearing. In other embodiments, lower gripping part 45 is affixed to sleeve body 11 with glue, heat bonding, or the like.

Lower gripping part 45 is applied to, and extends across, foot-receiving sleeve 26 of sleeve body 11 between ankle-receiving sleeve 25 and lower end 21 formed with toe opening 33 at a contact area, which is denoted generally at 56". Contact area 56" is defined by outer surface 50" and extends between top and bottom marginal edges 52" and 54" of lower gripping part 45, and from side marginal edge 51" of lower gripping part 45 at side portion 14 of sleeve body 11 and along front portion 12 of sleeve body 11 to opposed side marginal edge 52" of lower gripping part 45 at side portion 15 of sleeve body 11. There is a gap 60" between opposed side marginal edges 51" and 52" of lower gripping part 45 exposing therebetween rear portion 13 of foot-receiving sleeve 26 of sleeve body 11 between ankle-receiving sleeve 25 and lower end 21 as shown in FIG. 7. Gap 60" is free of lower gripping part 45. Because lower gripping part 45 is formed of a gripping material that has the tacky/gripping material characteristic as described above, outer surface 50" of lower gripping part 45 is slightly sticky or adhesive so as to have a tacky/gripping property or otherwise a tacky/gripping material characteristic as is typical of PVC vinyl, that grippingly engages a surface, such as a metal surface, so that the touched surface resists slipping across lower gripping part 45 when in direct contact with lower gripping part 45, and yet lower gripping part 45 does not leave a sticky or adhesive residue on the surface it engages or touches. Lower gripping part 45 is formed with perforations 65" such that lower gripping part 45 is perforated to provide vapor transmission from sleeve body 11 through inner surface of lower gripping part 45 to outer surface 50.

Figure 8:
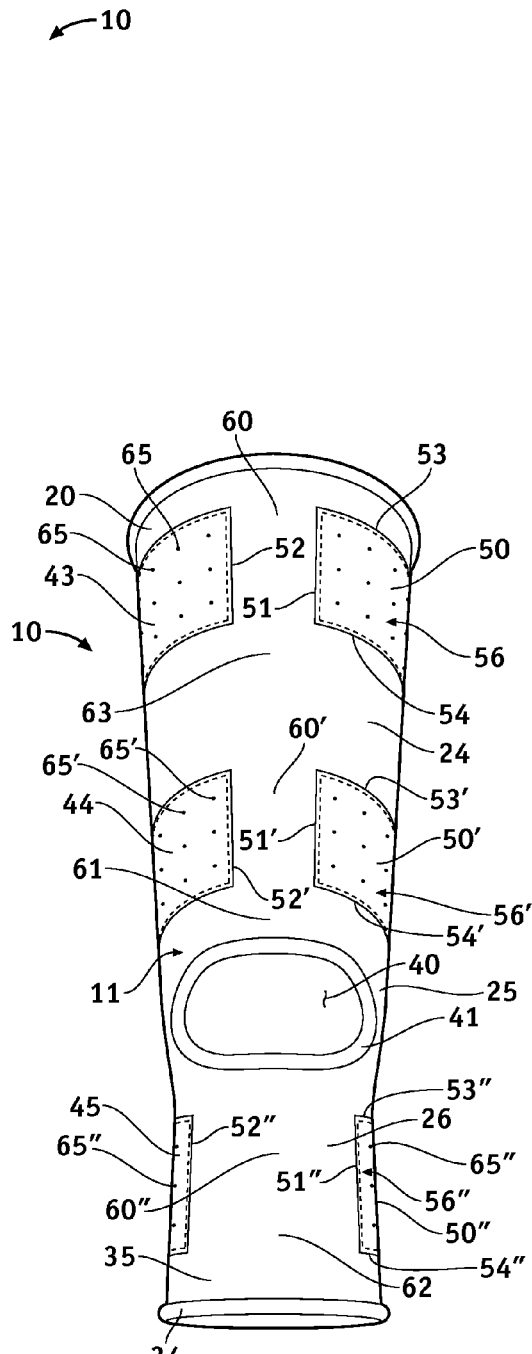
FIG. 8 is a bottom rear perspective view of the embodiment of FIG. 1.

Gaps 60, 60', and 60" are aligned longitudinally along rear portion 13 of sleeve body 11. With reference now to FIGS. 7 and 8, leg-receiving sleeve 24 of sleeve body 11 is free from and unconcealed by upper and intermediate gripping parts 43 and 44 along rear portion 13, defining a path 61 extending along rear portion 13 of sleeve body 11 from upper end 20 to heel opening 40 including gap 60 between opposed side marginal edges 51 and 52 of upper gripping part 43 and gap 60' between opposed side marginal edges 51' and 52' of intermediate gripping part 44. Likewise, foot-receiving sleeve 26 of sleeve body 11 is free from and unconcealed by lower gripping part 45 along rear portion 13, defining a second path or sole 62 extending along rear portion 13 of sleeve body 11 from lower end 21 to heel opening 40 including gap 60" between opposed side marginal edges 51" and 52" of lower gripping part 45. Path 61 and sole 62 together define a strip 63 of sleeve body 11 providing a smooth, non-tacky surface extending between opposed upper and lower ends 20 and 21.

According to the principle of the invention, garment 10 is used to cloth a lower appendage of a performer, such as a pole-dancing performer. Garment 10 is suitable for wearing on either a left or right human lower appendage and a garment constructed and arranged in accordance with the principle of the invention may be worn on either one of or both of the lower appendages of a performer. As a matter of example, FIG. 9 illustrates two garments 10 worn by the respective lower appendages of a performer.

Figure 9:
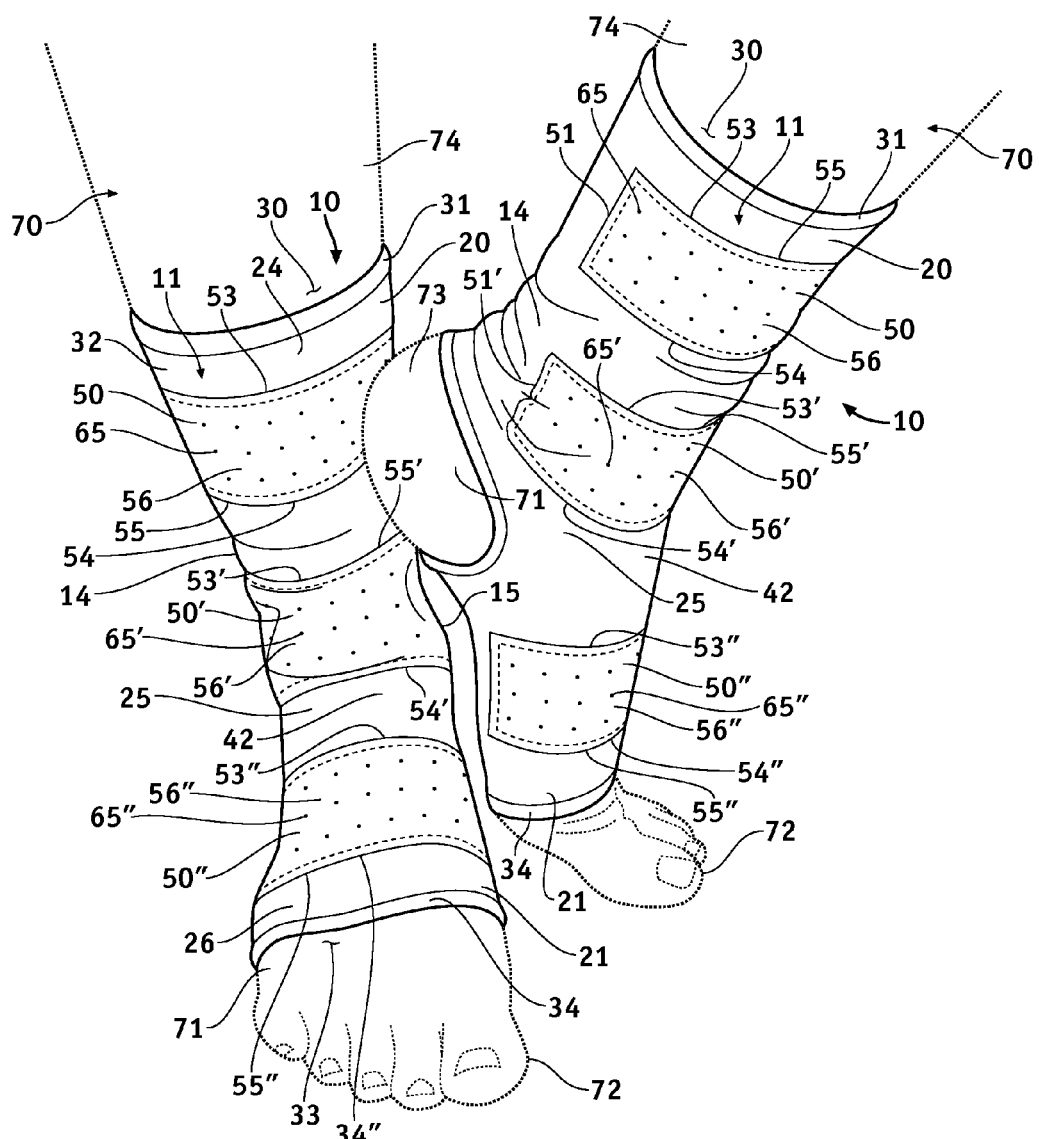
FIG. 9 illustrates garments each constructed and arranged in accordance with the garment of FIG. 1 shown as they would appear being worn on the lower extremities of a performer.

To apply garment 10 to a human lower appendage from a free or uninstalled condition, as shown in FIG. 1, to a worn condition on a performer's lower appendage, as shown in FIG. 9, garment 10 is put on much like how one would put on a conventional sock, in that garment 10 is taken up by hand and held at upper end 20 with front portion 12 facing forwardly relative to the performer and mouth 30 at upper end 20 is held open so as to present volume 16 bound by sleeve body 11 to receive a performer's foot 71 of lower appendage 70. The lower appendage 70 is then applied toes 72 first into volume 16 of garment 10 by introducing the performer's toes 72 of foot 71 to volume 16 through mouth 30 as leg-receiving sleeve 24 is pulled upward in a longitudinal direction over toes 72 and over the foot. Because sleeve body 11 is constructed of a material and in such a fashion as to resist stretching in the longitudinal direction, stretching in the longitudinal direction is limited to facilitate a user pulling garment 10 on so as to advance leg-receiving sleeve 24 up performer's lower appendage 70 in response to performer's pulling in the longitudinal direction in a direction up the performer's leg. Garment 10 is so pulled and advanced over the lower appendage 70, which is, in turn, pushed into and through volume 16 of garment 10 as garment is pulled on. Foot 71 enters volume 16 through mouth 30 as performer continues to pull garment 10 upward in a longitudinal direction and push her foot 71 into and through garment 10, and garment 10 is so advanced over the performer's heel 73. Because garment 10 is constructed of a material and in such a fashion as to allow elastic stretching radially, sleeve body 11 expands to accommodate the size of performer's foot 71 and heel 73. Indeed, because garment 10 is constructed of a material and in a fashion so as to allow elastic stretching radially in a direction that is perpendicular relative to the length of sleeve body 11 from upper end 20 to lower end 21, sleeve body 11 is capable of elastically expanding and contracting in the radial direction relative to the longitudinal direction of sleeve body 11 to accommodate many different sizes of feet and heels. Toes 72 continue to pass through volume 16 from upper end 20 to lower end 21, past heel opening 40, and garment 10 is so advanced past performer's ankle and onto leg 74 between the heel and knee of the lower appendage 70, whereby leg 74 is received in, or otherwise applied to, leg-receiving sleeve 24, the performer's ankle is received in, or otherwise applied to, ankle-receiving sleeve 25, and foot 71 is received in, or otherwise applied to foot-receiving sleeve 26, arranging garment 10 in the worn condition and ready for use. With front portion 12 facing forwardly relative to the performer during this installation procedure, front portion 12 formed with upper, intermediate, and lower gripping parts 43, 44, 45 are applied across and along the front or top of lower appendage 70, and rear portion 13 is applied across and along the bottom or backside of lower appendage 70. Although the process of moving garment 10 from a free condition to a worn condition is presented and described above as a series of sequential steps, it should be understood that the installation of garment 10 to lower appendage 70 is preferably accomplished in a single, continuous motion.

When so installed onto the leg 74, ankle, and foot 71 of the lower appendage 70 of a human performer as described, front portion 12 is applied to and across the top or front side of the performer's foot 71, ankle, and lower leg 74 between the ankle and the knee, rear portion 13 is applied to and across the bottom or backside of the performer's foot 71, ankle, and leg 74 between the ankle and the knee, and side portions 14 and 15 are applied to and across the opposed sides, respectively, of the performer's foot 71, ankle, and leg 74 between the ankle and the knee. In this orientation of garment 10 when installed on a performer lower extremity 70 as described, upper gripping part 43 of garment 10 is positioned near upper end 20 of sleeve body 11 between the performer's ankle and knee and extends across or otherwise wraps about the top or front side of the performer's leg 74 between the performer's ankle and knee from near the bottom or backside of the performer's leg 74 at one side of the performer's leg 74 to near the bottom or backside of the performer's leg 74 at the opposed side of the performer's leg 74. Intermediate gripping part 44 of garment 10 is positioned near ankle-receiving sleeve 25 between upper and lower ends 20 and 21 of sleeve body 11 adjacent to or otherwise near the performer's ankle and extends across or otherwise wraps about the top or front side of the performer's leg 74 adjacent to or otherwise near the performer's ankle from near the bottom or backside of the performer's leg 74 at one side of the performer's leg 74 to near the bottom or backside of the performer's leg 74 at the opposed side of the performer's leg 74. Lower gripping part 45 of garment 10 is, in turn, positioned near lower end 21 of garment 10 between the performer's ankle and toes 72 and extends across or otherwise wraps about the top or front side of the instep portion of performer's foot 71 from near the bottom or backside of the performer's foot 71 at one side of the performer's foot 71 to near the bottom or backside of the performer's foot 71 at the opposed side of the performer's foot 71.

And so lower appendage 70 is applied toes 72 first into volume 16 through mouth 30 while garment 10 is held front portion 12 up or forward relative to the performer and garment 10 is pulled upwardly along lower appendage 70 over the performer's foot 71 and ankle and to leg 74 between the performer's ankle and knee. In the worn condition, a length of leg 74 between the performer's ankle and knee is girdled by leg-receiving sleeve 24, the performer's ankle is girdled by ankle-receiving sleeve 25, the instep region or portion of the performer's foot 71 between the ankle and toes 72 is girdled by foot-receiving sleeve 26, toes 72 of foot 71 extend outwardly through and forwardly of toe opening 33, and heel 73 of foot 71 is located in and extends through heel opening 40. Front portion 12 of leg-receiving sleeve 24 extends between ankle-receiving sleeve 25 and upper end 20 of sleeve body 11 and is applied over and across the front of the leg 74 girdled by leg-receiving sleeve 24, and rear portion 13 of leg-receiving sleeve 24 extends between ankle-receiving sleeve 25 and upper end 20 of sleeve body 11 and is applied over and across the rear of the leg 74 girdled by leg-receiving sleeve 74. Front portion 12 of foot-receiving sleeve 26 extends between ankle-receiving sleeve 25 and lower end 21 of sleeve body 11 and is applied over and across the top or front of the foot 71 girdled by foot-receiving sleeve 26, and rear portion 13 of foot-receiving sleeve 26 extends between ankle-receiving sleeve 25 and lower end 21 of sleeve body 11 and is applied over and across the rear, bottom, or backside of the foot 71 girdled by foot-receiving sleeve 76.

In this installation of garment 10, upper gripping part 43, which is circumferentially located upon and about outer surface 23 of leg-receiving sleeve 24 of sleeve body 11 near upper end 20 and which extends across outer surface 23 of front portion 12 leg-receiving sleeve 24 of sleeve body 11 from side portion 14 near rear portion 13 to side portion 15 near rear portion 13, girdles leg 74 between the ankle and knee such that it circumferentially runs across the front of leg 74 from side marginal edge 51 of upper gripping part 43 near side portion 14 near rear portion 13 of leg-receiving sleeve 24 of sleeve body 11 applied along the rear of leg 74 along one side of leg 74 to side marginal edge 52 of upper gripping part 43 near side portion 15 of upper gripping part 43 near rear portion 13 of leg-receiving sleeve 24 of sleeve body 11 applied along the rear of leg 74 along the opposed side of leg 74. Intermediate gripping part 44, which is circumferentially located upon and about outer surface 23 of leg-receiving sleeve 24 of sleeve body 11 near ankle-receiving sleeve 25 and between ankle-receiving sleeve 25 and upper gripping part 43 and which extends across outer surface 23 of front portion 12 of leg-receiving sleeve 24 of sleeve body 11 from side portion 14 near rear portion 13 to side portion 15 near rear portion 13, girdles leg 74 near the performer's ankle such that it circumferentially runs across the front of leg 74 near and just above the performer's ankle from side marginal edge 51' of intermediate gripping part 44 near side portion 14 near rear portion 13 of leg-receiving sleeve 24 of sleeve body 11 applied along the rear of leg 74 along one side of leg 74 near and just above the performer's ankle to side marginal edge 52" of intermediate gripping part 44 near side portion 15 near rear portion 13 of leg-receiving sleeve 24 of sleeve body 11 applied along the rear of leg 74 along the opposed side of leg 74 near and just above the performer's ankle. Finally, lower gripping part 45, which is circumferentially located upon and about outer surface 23 of foot-receiving sleeve 26 of sleeve body 11 near ankle-receiving sleeve 25 and between ankle-receiving sleeve 25 and lower end 21 of sleeve body 11 and which extends across outer surface 23 of front portion 12 of foot-receiving sleeve 26 of sleeve body 11 from side portion 14 near rear portion 13 to side portion 15 near rear portion 13, girdles the instep portion of foot 71 such that it circumferentially runs across the top or front of foot 71 between the performer's ankle and toes 72 from side marginal edge 51" of lower gripping part 45 near side portion 14 near rear portion 13 of foot-receiving sleeve 26 of sleeve body 11 applied along bottom of foot 71 along one side of foot 71 to side marginal edge 52" of lower gripping part gripping part 45 near side portion 15 near rear portion 13 of foot-receiving sleeve 26 of sleeve body 11 applied along the bottom of foot 71 along the opposed side of foot 71. With this installation of garment 10 with respect to lower appendage 70, upper and intermediate gripping parts 43,44 are applied to the front of leg 74 of the performer's lower appendage 70 and lower gripping part 45 is applied to the top of front of foot 71 of the performer's lower appendage 70 such that upper, intermediate, and lower gripping parts 43,44,45 positioned frontally or forwardly along the top, front or forward region of the performer's lower appendage 70 making such upper, intermediate, and lower gripping parts 43,44,45 available for gripping in a direction from the front of the performer's lower appendage 70, which is particularly useful for pole-dancing activities.

The stretch or elastically constrictive characteristic imparted by the stretch material and construction of sleeve body 11, and the receipt of lower appendage 70 within volume 16, cooperate with heel opening 40 held on heel 73 to hold garment 10 in place on performer's lower appendage 70 in the worn condition. Other conventional methods of application exist and should be apparent. To easily remove garment 10, one must merely pull lower end 21 of garment 10 in a direction opposite to that required to apply garment 10 to lower appendage 70. Alternatively, garment 10 is rolled downwardly upon itself from upper end 20 to lower end 21 at toes 72 and then pulled off foot 71. Other conventional methods of removal exist and should be apparent.

In the worn condition, garment 10 can be used for any desired purpose or action, but is particularly suitable in pole-dancing activity and training, in which garment 10 allows performer to train longer, more effectively, and with less risk of injury than would otherwise be possible, for reasons explained herein. Garment 10 provides overlying and protective resistance to performer's lower appendage 70 from bruising, burning, rubbing, and other effects caused by contact of performer's lower appendage 70 against a metal pole. With garment 10 applied to performer's lower appendage 70 in the worn condition, contact areas 56, 56', and 56" relate to "hot" points of tops/fronts of leg 74 and foot 71 making garment 10 uniquely structured to assist performer in pole-dancing activity to allow performer to grip the pole in a direction along the top/front and sides of performer's leg 74 and foot 71 of lower appendage 70, in accordance with the principle of the invention. In pole-dancing activities, contact areas 56, 56', and 56" are placed against the pole and used as leverage points at which force or torque is applied from lower appendage 70 to the pole. The compressible radial thickness of sleeve body 11 provides cushioning, and sleeve body 11, together with upper gripping part 43, intermediate gripping part 44, and lower gripping part 45 overlying sleeve body 11, protects lower appendage 70 from bruising, burning, rubbing, and other effects caused by pole-dancing activities, allowing performer to train and resist fatigue and injury longer than compared to when no garment 10 is worn. Moreover, toes 72 at lower end 21, heel 73 at heel opening 40, and leg 74 at upper end 20, allow performer to retain tactile qualities provided by a bare foot 71 while benefiting from the protective and grip qualities of garment 10 covering the remainder of lower appendage 70. Strip 63 defined by gaps 60,60',60" along rear portion 13 of sleeve body 11 also provides a smooth, non-tacky surface extending from upper end 20 to lower end 21 of garment 10, providing performer a longitudinal area extending from upper end 20 to lower end 21 that does not grippingly engage a metal pole. The deformable, pliant, elastic, and elastically constrictive material characteristics of garment 10, and the deformable, pliant, and flexible material characteristics of gripping parts 43,44,45, permit garment 10, including gripping parts 43,44,45, to yield and deform in response to performer movement, and tends to hold garment 10 in place on the performer without restricting user movement.

Although the assistive and protective garment 10 set forth in this disclosure is particularly useful in pole dance activities, garment 10 is equally usefully in assisting and protecting a user during other activities, such as sports activities, gymnastics and especially balance beam gymnastics activities, exercising activities, and the like, where a user may come into contact with sports, gymnastics, and exercising equipment or implements.

Figure 10:
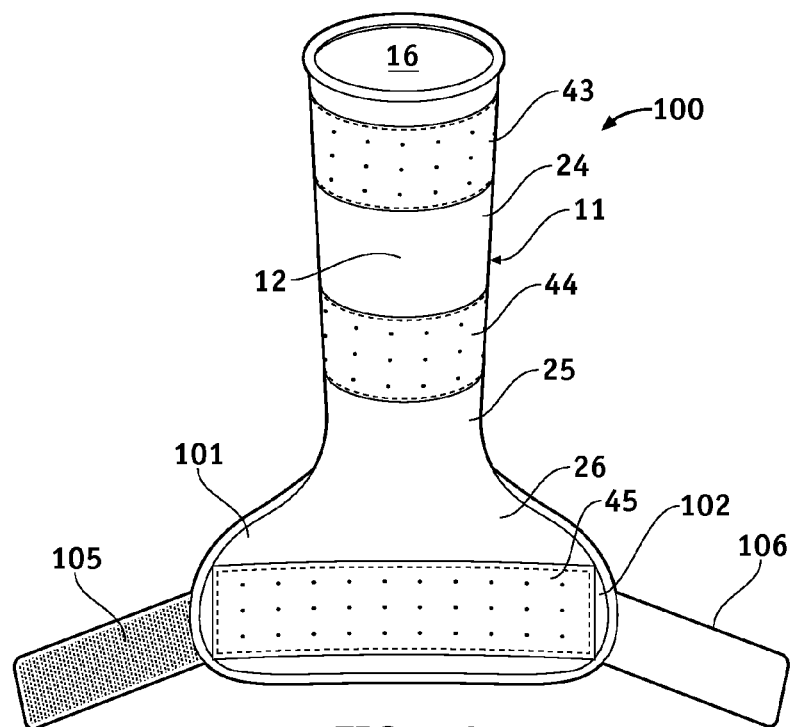
FIG. 10 is a front perspective view of an alternate embodiment of an assistive and protective garment constructed and arranged in accordance with the principle of the invention.
Figure 11:
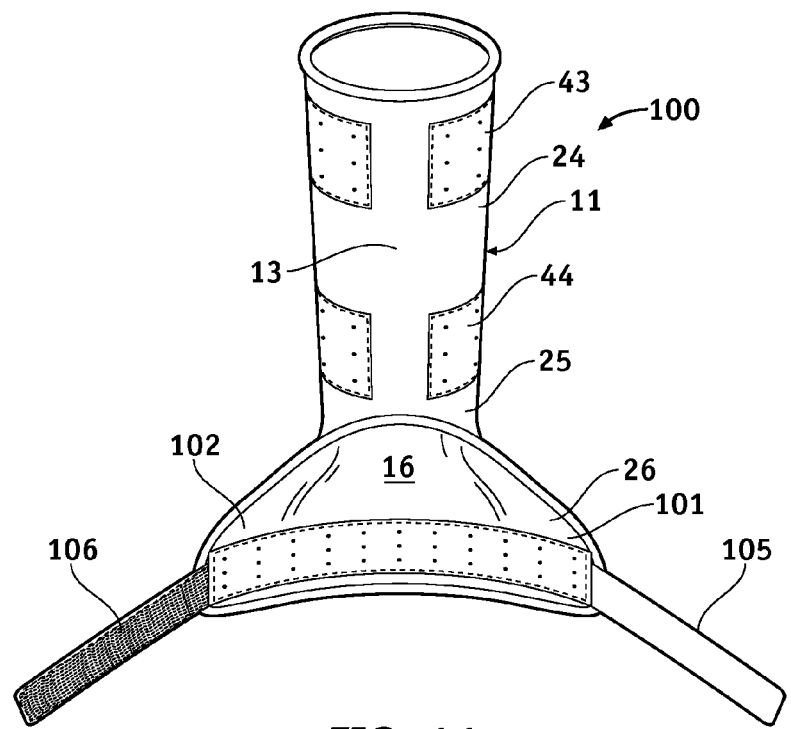
FIG. 11 is a rear perspective view of the embodiment of FIG. 10.

Attention is now directed to FIGS. 10-14, in which there is illustrated an assistive and protective garment 100 for use in exercising, sports, gymnastics, pole dance activities, and the like. In common with garment 10, garment 100 shares sleeve body 11 including front and rear portions 12 and 13 and also volume 16, leg-receiving sleeve 24, ankle-receiving sleeve 25, foot-receiving sleeve 26, and upper, intermediate, and lower gripping parts 43,44,45, and is identical in every respect to garment 10 with the exception that in garment 100 foot-receiving sleeve 26 is severed along rear portion 13 from heel opening 40 of ankle-receiving sleeve 25 to outer end 21 of sleeve body 11 forming in ankle-receiving and foot-receiving sleeves 25,26 opposed flaps 101 and 102 in the respective side portions 14 and 15 of sleeve body 11. Flaps 101 and 102 move between an open position as shown in FIGS. 10 and 11 defining an open position of foot-receiving sleeve 26, and a closed position as shown in FIG. 13 to girdle a foot. An engagement assembly is formed in flaps 101 and 101, and is used to secure flaps 100 and the closed position as in FIGS. 13 and 14. The engagement assembly includes opposed hook and loop straps of a hook-and-loop assembly of a type commonly found under the VELCRO trademark, including a hook strap 105 attached and secured to flap 101, and a corresponding loop strap 106 attached and secured to flap 102. Leg-receiving sleeve 24 is applied to leg 74 of performer lower extremity 70 as shown in FIGS. 12-14 in the way and manner previously-described in conjunction with garment 10. In garment 100, flaps 100 and 101 can be opened as shown in FIG. 12 to make pulling garment 100 onto leg 74 a bit easier, particularly if the performer is wearing a shoe 110 on her foot 71 as shown. After slipping leg 74 into and through leg-receiving 24 as shown in FIG. 12, from the open position of flaps 100 and 101 as shown they may be folded downwardly on either side of foot 71 into the closed position as shown in FIG. 13 so as to girdle foot 71 and also shoe 110 in this example, and hook and loop straps 105 and 106 may be folded under shoe 100 and overlapped and pressed together releasably securing hook strap 105 to loop strap 106 as shown in FIG. 14 thereby releasably securing flaps 101 and 102 in the closed position. At this point, garment 100 may be put to use in the manner described in conjunction with garment 10. One need only pull hook and loop straps 105 and 106 apart in order to move foot-receiving sleeve 26 from the closed position of flaps 101 and 102 to the open position of flaps 101 and 102, such as for taking garment 100 off.

It is to be understood although hook strap 105 is attached and secured to flap 101 and corresponding loop strap 106 attached and secured to flap 102, the relative positioning of hook and loop straps 105 and 106 can be reversed. Hook and loop straps 105 and 106 are exemplary of an engagement pair including an element there in the form of hook strap 105 and a complemental element thereof in the form of loop strap 106. Consistent with this disclosure, other forms of mutual or corresponding engagement pairs can be used to close flaps 101 and 102 to girdle a foot of a performer, such as a snap engagement pair, a button engagement pair, a clasp engagement pair, or the like.

Garments 10 and 100 are sized and constructed to fit onto a performer lower extremity or appendage as described, including the foot and the ankle and reaching to the leg to and between the ankle and knee of the human lower extremity or appendage. A garment constructed and arranged in accordance with the principle of the invention may be sized and constructed to fit onto other portions of the lower extremity or appendage of a performer, such as the region in and around the knee of a lower extremity or appendage of a user, and such a garment is illustrated in FIGS. 15-18 and is denoted generally at 120.

Referencing FIGS. 15 and 16 in relevant part, garment 120 is an assistive and protective garment for use in exercising, sports, gymnastics, pole dance activities, and the like. Like garments 10 and 120, garment 120 is a close-fitting garment in the form of a sleeve or sleeve body 121 for closely receiving a human lower appendage, including the knee region defined as the knee reaching to the lower thigh and the upper leg on either side of the knee of a human lower appendage. Sleeve body 121 is a kneepad garment worn on the knee to protect it against impact injury during, e.g., a fall or a strike, or to provide padding for extended kneeling. Sleeve body 121 is a tube or tubular garment that includes a front or front portion 130 and an opposing rear or rear portion 131, opposed sides or side portions 132 and 133, an upper end 140, which is open to admit a body part therethrough, and an opposing lower end 141, which is also open to admit a body part therethrough. Opposed front and rear portions 130 and 131 and opposed side portions 132 and 133 of sleeve body 121 extend along the entire length of sleeve body 121 from upper end 140 of sleeve body 121 to lower end 141 of sleeve body 121. Sleeve body 121 tapers somewhat from upper end 140 to lower end 141, and side 132 is the right side of sleeve body 121, and side 133 is the left side of sleeve body 121. Sleeve body 121 further includes opposed inner and outer surfaces 142 and 143 that extend along the entire length of sleeve body 121 from upper end 140 to lower end 141. Front and rear portions 130 and 131, and side portions 132 and 133 of the sleeve body 121 tube or tubular garment are formed integrally with each other and define the inner and outer surfaces 142 and 143 of sleeve body 121, all of which extend from upper end 140 of sleeve body 121 to lower end 141 of sleeve body 121. Inner surface 142 of sleeve body 121 bounds or otherwise defines volume 146 through sleeve body 121 from upper end 140 to lower end 141 to receive therein a knee and part of the thigh and leg on either side of the knee of the lower appendage of a human performer. Volume 146 is a body-receiving volume that extends through sleeve body 121 from upper end 140, which is open, to lower end 141, which is also open. When installed onto a body appendage, such as the knee region of the lower appendage or extremity of a human performer, the applied body appendage is applied to volume 146 and front portion 130 is applied to and across the top or front side of the performer's knee region, rear portion 131 is applied to and across the bottom or backside of the performer's knee region, and side portions 132 and 133 are applied to and across the opposed sides, respectively, of the performer's knee region.

Sleeve body 121 includes/defines body-receiving parts or portions including a thigh- and leg-receiving parts or portions formed in either side of a knee-receiving part or portion. The thigh-receiving part or portion is a sleeve, sleeve segment, or sleeve part 150 of sleeve body 121, the leg-receiving part or portion is a sleeve, sleeve segment, or sleeve part 152 of sleeve body 121, and the knee-receiving part or portion is a sleeve, sleeve segment, or sleeve part 151 of sleeve body 121 located between sleeves 150 and 152 at an intermediate location of sleeve body 121 between upper and lower ends 140 and 141. Sleeves 150, 151, and 152 are similar in structure and are segments or parts of the entire sleeve that makes up sleeve body 121. In this regard, sleeve body 121 is considered a major sleeve, and sleeves 150,151,151 defining the thigh-, knee-, and leg-receiving parts that make up sleeve body 121 are integrally formed together and are considered minor sleeves of sleeve body 121.

Thigh-receiving sleeve 150 receives and accommodates a portion of the thigh of a human performer between the knee and the hip and has a thigh opening or mouth 160 at upper end 140 of sleeve body 121 that defines the open characteristic of upper end 140. Thigh-receiving sleeve 150 extends from mouth 160 to knee-receiving sleeve 151. Mouth 160 is defined by a lip 161 formed in upper end 140 of sleeve body 121. Lip 161 encircles and defines mouth 160, which leads to or otherwise into volume 146 bound by sleeve body 121 at upper end 140 of sleeve body 121. Lip 161 is an annular band formed of conventional elastic band material having deformable, elastic, and size- and shape-memory material characteristics, which cause lip 161 to tend to elastically constrict inwardly in a radial direction against a thigh that has been applied to thigh-receiving sleeve 150. As the term is used here, "radial" means generally directed along a line extending inwardly and outwardly relative to a center of volume 146 bound by sleeve body 121 and through sleeve body 121. Thigh-receiving sleeve 150 of sleeve body 121 is characterized in that it is a continuous sidewall 162 that extends between mouth 160 and knee-receiving sleeve 151. Sidewall 162 of thigh-receiving sleeve 150 of sleeve body 121 encircles volume 146 between upper end 140 and knee-receiving sleeve 151 and girdles a performer's thigh near the knee between the knee and the hip of the human lower appendage/extremity.

Leg-receiving part or sleeve 152 receives and accommodates a leg of the lower appendage of a human performer, and has a leg opening or mouth 163 at lower end 141 of sleeve body 121 that defines the open characteristic of lower end 141 of sleeve body 121. Leg-receiving sleeve 152 extends from leg opening 163 to knee-receiving sleeve 152. Leg opening 163 is defined by a lip 164 formed in lower end 141 of sleeve body 121. Lip 141 encircles and defines leg opening 163, which leads to or otherwise into volume 146 bound by sleeve body 121 at lower end 141 of sleeve body 121. Lip 164 is an annular band formed of conventional elastic band material having deformable, elastic, and size- and shape-memory material characteristics, which cause lip 164 to tend to elastically constrict inwardly in a radial direction against a leg that has been applied to leg-receiving sleeve 152. Leg-receiving sleeve 152 is characterized in that it is a continuous sidewall 165 that extends between leg opening 163 and knee-receiving sleeve 151. Sidewall 165 encircles volume 146 between lower end 141 and knee-receiving sleeve 151 and girdles a portion of a leg applied to volume 146 near the knee between the knee and the ankle of the human lower appendage/extremity.

Knee-receiving sleeve 151 accommodates a knee of the lower appendage of a human performer, and extends between thigh-receiving sleeve 150 and leg-receiving sleeve 152. Knee-receiving sleeve 151 is formed with a knee opening 170 located along and through rear portion 131 of sleeve body 121 at a generally intermediate location with respect to knee-receiving sleeve 151 to expose the back of the knee, e.g. the popliteal fossa, of a human lower appendage/extremity. Knee opening 170 is defined by a lip 171. Lip 41 encircles and defines knee opening 170 and leads to or otherwise into volume 146 bound by sleeve body 121 at knee-receiving sleeve 151 in a direction from rear portion 131. Lip 171 is an annular band formed of conventional elastic band material having deformable, elastic, and size- and shape-memory material characteristics, which cause lip 171 to tend to elastically constrict inwardly in a radial direction. Knee-receiving sleeve 151 has an otherwise continuous sidewall 172 formed with heel opening 170 between thigh-receiving sleeve 150 and leg-receiving sleeve 152. Sidewall 172 encircles volume 146 between thigh-receiving sleeve 150 and leg-receiving sleeve 152 and girdles the knee to volume 146 between thigh-receiving sleeve 150 and leg-receiving sleeve 152. Front portion 130 of sleeve body 121 of garment 120 is formed with a conventional knee pad 174, which opposes and is located opposite to knee opening 170 and rear portion 131. Knee pad 174 is soft and flexible and extends in a longitudinal direction along front portion 130 from thigh-receiving sleeve 150 and across knee-receiving sleeve 151 and to leg-receiving sleeve 152, and extends laterally across knee-receiving sleeve 151 from side portion 132 to side portion 133, extends laterally across a portion of thigh-receiving sleeve 150 near knee-receiving sleeve 151 from side portion 132 to side portion 133, and further extends laterally across a portion of leg-receiving sleeve 152 near knee-receiving sleeve 151 from side portion 132 to side portion 133.

Sleeve body 121 is constructed of the same material as sleeve body 11 of garment 10, and the details of the material of sleeve body 11 applies in every respect to sleeve body 121 are will not be discussed again in detail in connection with garment 120. And so consistent with the discussion of garment 10, sleeve body 121 is constructed from a 2-way stretch fabric/textile that is woven, knitted, or otherwise arranged in a common and well-known weave pattern so as to resists lengthwise stretching in a longitudinal direction from upper end 140 to lower end 141, and that elastically stretches and constricts radially in a crosswise direction perpendicular to the described longitudinal direction allowing sleeve body 121 to elastically circumferentially expand and contract to so as to accommodate many different sizes of legs, ankles, and feet. As the terms are used here, "longitudinal" means generally directed along a direction extending between upper and lower ends 140 and 141 of garment 120. Sleeve body 121 has a thickness in the radial direction which is compressible. Outer surface 143 of sleeve body 121 is smooth so as to pass freely over surfaces such as metal.

In accordance with the principle of the invention, garment 120 is formed with and carries a plurality of exterior gripping parts. These gripping parts are, more specifically, surface-gripping parts, which are located exteriorly and which are useful for gripping surfaces against which they are applied. And so when garment 120 is worn, the gripping parts or surface-gripping parts applied exteriorly to garment 120 may be applied against surfaces to assist a user in maneuvering upon and against such surfaces. In garment 120, the gripping parts include two, separate gripping parts, including an upper gripping part 180 and an opposed lower gripping part 181. Upper and lower gripping parts 180 and 181 are tack strips and are applied exteriorly to outer surface 23 of sleeve body 21 along rear portion 131 so as to be available for gripping surfaces they come in contact with in a direction toward rear portion 131 tending to cause gripping parts 180,181 to resist slipping across surfaces against which they are applied in a direction toward rear portion 131 as described above in connection the gripping parts of garment 10.

Upper gripping part 180 and lower gripping part 181 are spaced-apart and separate from one another. Upper gripping part 181 is carried by thigh-receiving sleeve 150 near upper end 140 between upper end 140 and knee-receiving sleeve 151 including knee opening 170 and, moreover, between upper end 140 and knee pad 174. Lower gripping part 181 is carried by leg-receiving sleeve 152 near lower end 141 between lower end 141 and knee-receiving sleeve 151 including knee opening 170 and, moreover, between lower end 141 and knee pad 174. Upper gripping part 180 and lower gripping part 181 are carried by sleeve body 121 and are considered a part of, or otherwise an extension of, sleeve body 121, but are made of a material that is different from the material of sleeve body 121 so as to provide the gripping function as disclosed herein, which is a function that the material of sleeve body 121 does not provide.

Upper gripping part 180 and lower gripping part 181 are substantially coextensive being substantially equal in size and in shape, and are each a flat, elongate strip of material having the properties of flexibility, pliancy, inelasticity, and tackiness, which means that they are each slightly sticky or adhesive in nature that grip surfaces they come in contact with and resist slipping without leaving a resulting residue on touched objects. Preferably, upper and lower gripping parts 180,181 are, like upper, intermediate, and lower gripping parts 43,44, 45 of garments 10 and 100, fashioned of PVC vinyl.

Upper gripping part 180 is circumferentially located upon and about outer surface 143 of sleeve body 121 near upper end 140 and extends across outer surface 143 of rear portion 131 of sleeve body 121 from side portion 132 near front portion 130 to side portion 133 near front portion 130. Lower gripping part 181 is, identically to that of upper gripping part 180, circumferentially located upon and about sleeve body 121 near lower end 141 and extends across outer surface 143 of rear portion 131 of sleeve body 121 from side portion 132 near front portion 130 to side portion 133 near front portion 130. Upper and lower gripping parts 180,181 extend across outer surface 143 of rear portion 131 of sleeve body 121 as described in a transverse direction relative to the longitudinal direction of sleeve body 121 extending from upper end 140 to lower end 141 of sleeve body 121.

Upper gripping part 180 includes an inner surface (not shown) applied directly to outer surface 143 of sleeve body 121, and an opposing, exposed outer surface 190 for surface gripping. Upper gripping part 180 is formed with opposed, parallel side marginal edges 191 and 192, and opposed, parallel top and bottom marginal edges 193 and 194, which together cooperate to form a perimeter 195 bounding/encircling the inner surface (not shown) and the outer surface 190 of upper gripping part 180. Upper gripping part 180 is affixed directly to outer surface 143 of sleeve body 121 by stitching applied along perimeter 195 between upper gripping part 180 and sleeve body 121. The stitching is preferably nylon stitching or the like that is strong, resilient, and resistant to tearing. In other embodiments, upper gripping part 180 is affixed to sleeve body 121 with glue, heat bonding, or the like.

Upper gripping part 180 is applied to and carried by and extends across thigh-receiving sleeve 150 of sleeve body 121 at a contact area, which is denoted generally at 196. Contact area 196 is defined by outer surface 190 and extends between top and bottom marginal edges 193 and 194 of upper gripping part 180, and from side marginal edge 191 of upper gripping part 180 at side portion 132 of sleeve body 121 and along rear portion 131 of sleeve body 121 to opposed side marginal edge 192 of upper gripping part 180 at side portion 133 of sleeve body 121. There is a gap 200 between opposed side marginal edges 191 and 192 of upper gripping part 180 exposing therebetween front portion 130 of sleeve body 121 as shown in FIG. 16. Because upper gripping part 180 has the tacky/gripping material characteristic as described above, outer surface 190 of upper gripping part 180 is slightly sticky or adhesive so as to have a tacky/gripping property or otherwise a tacky/gripping material characteristic as is typical of PVC vinyl, that grippingly engages a surface, such as a metal surface, so that the touched surface resists slipping across upper gripping part 180 when in direct contact with upper gripping part 180, and yet upper gripping part 180 does not leave a sticky or adhesive residue on the surface it directly engages or touches. Upper gripping part 180 is formed with perforations 197 such that upper gripping part 180 is perforated to provide vapor transmission from sleeve body 121 through inner surface of upper gripping part 180 to outer surface 190.

With the exception of their respective locations on sleeve body 121, lower gripping part 181 is identical in every respect to upper gripping part 180, and the foregoing discussion of upper gripping part 180 applies equally to lower gripping part 181. For reference purposes, common reference characters used to describe the features of upper gripping part 180 are also used to denote the features of lower gripping part 181, and, for clarity, incorporate a prime ("'") for the features of lower gripping part 181.

In common with upper part 180, lower gripping part 181 is circumferentially located about sleeve body 121 and shares inner surface, outer surface 190', opposed side marginal edges 191' and 192', opposed top and bottom marginal edges 193' and 194', perimeter 195' bounding outer surface 190', the defined contact area 196' and gap 200' exposing front portion 130 of sleeve body 121 between opposed side marginal edges 191' and 192', and also perforations 197'.

Lower gripping part 181 is circumferentially located upon and about outer surface 143 of sleeve body 121 near lower end 141 and extends across outer surface 143 of rear portion 131 of sleeve body 121 from side portion 132 near front portion 130 to side portion 133 near front portion 130. Lower gripping part 181 includes an inner surface (not shown) applied directly to outer surface 143 of sleeve body 121, and an opposing, exposed outer surface 190' for surface gripping. Lower gripping part 181 is formed with opposed, parallel side marginal edges 191' and 192', and opposed, parallel top and bottom marginal edges 193' and 194', which together cooperate to form perimeter 195' bounding/encircling the inner surface (not shown) and the outer surface 190' of lower gripping part 181. Lower gripping part 181 is affixed directly to outer surface 143 of sleeve body 121 by stitching applied along perimeter 195' between lower gripping part 181 and sleeve body 121. The stitching is preferably nylon stitching or the like that is strong, resilient, and resistant to tearing. In other embodiments, lower gripping part 181 is affixed to sleeve body 121 with glue, heat bonding, or the like.

Lower gripping part 181 is applied to and carried by and extends across leg-receiving sleeve 152 of sleeve body 121 at a contact area, which is denoted generally at 196'. Contact area 196' is defined by outer surface 190' and extends between top and bottom marginal edges 193' and 194' of lower gripping part 181, and from side marginal edge 191' of lower gripping part 181 at side portion 132' of sleeve body 121 and along rear portion 131 of sleeve body 121 to opposed side marginal edge 192' of lower gripping part 181 at side portion 133 of sleeve body 121. There is gap 200' between opposed side marginal edges 191' and 192' of lower gripping part 181 exposing therebetween front portion 130 of sleeve body 121 as shown in FIG. 16. Because lower gripping part 181 has the tacky/gripping material characteristic as described above, outer surface 190' of lower gripping part 181 is slightly sticky or adhesive so as to have a tacky/gripping property or otherwise a tacky/gripping material characteristic as is typical of PVC vinyl, that grippingly engages a surface, such as a metal surface, so that the touched surface resists slipping across lower gripping part 181 when in direct contact with lower gripping part 181, and yet lower gripping part 181 does not leave a sticky or adhesive residue on the surface it directly engages or touches. Lower gripping part 181 is formed with perforations 197' such that lower gripping part 181 is perforated to provide vapor transmission from sleeve body 121 through inner surface of lower gripping part 181 to outer surface 190'.

Gaps 200 and 200' are aligned longitudinally along front portion 130 of sleeve body 121, and sleeve body 121 is unconcealed by upper and lower gripping parts 180 and 181 along front portion 130 at gaps 200 and 200'. The portions of sleeve body 121 at gaps 200 and 200' are free the gripping parts 180 and 181 and are smooth and non-tacky surfaces.

According to the principle of the invention, garment 120 is used to cloth a lower appendage of a performer, such as a pole-dancing performer. Garment 120 is suitable for wearing on either a left or right human lower appendage and a garment constructed and arranged in accordance with the principle of the invention may be worn on either one of or both of the lower appendages of a performer. As a matter of example, FIGS. 17 and 18 illustrate garment 120 worn by lower extremity/appendage 70 of a performer.

Figure 17:
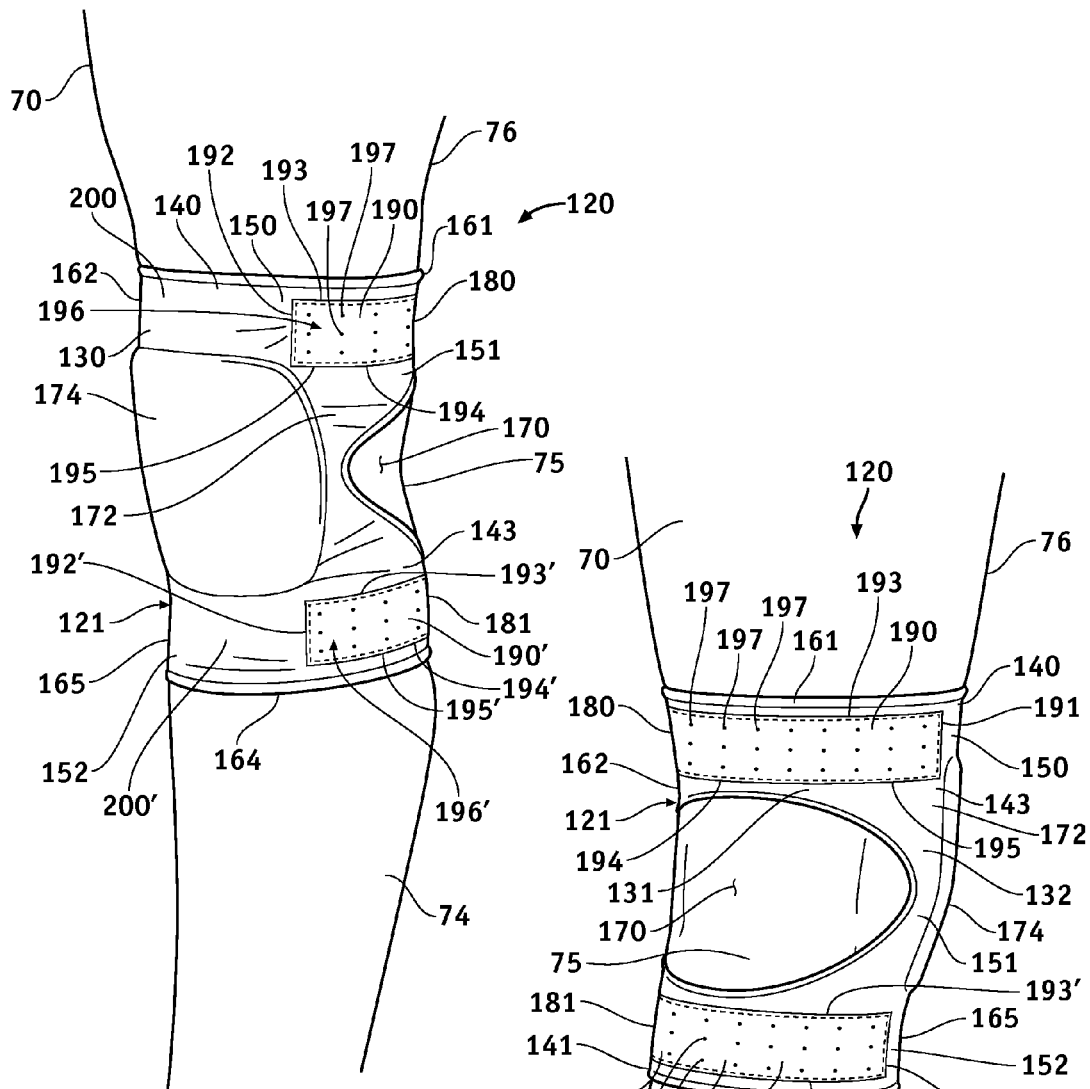
FIGS. 17 and 18 are perspective views of the embodiment of FIG. 15 shown as it would appear being worn on a lower extremity of a performer.
Figure 18:
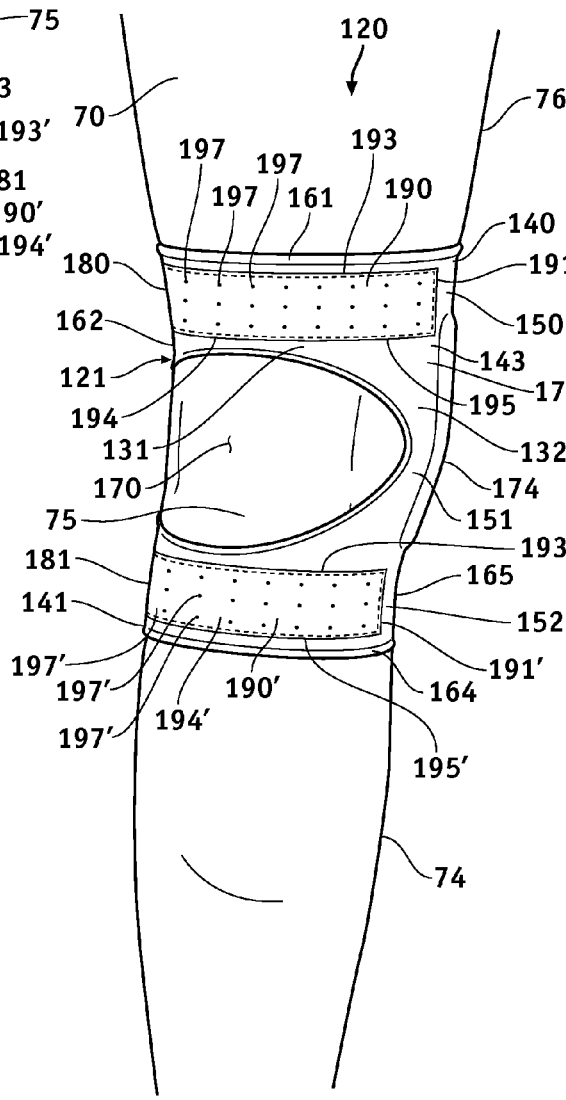

To apply garment 120 to a human lower appendage from a free or uninstalled condition, as shown in FIGS. 15 and 16, to a worn condition on a performer's lower appendage, as shown in FIGS. 17 and 18, garment 120 is put on much like how one would put on a conventional knee pad, in that garment 120 is taken up by hand and held at upper end 140 with front portion 130 facing forwardly relative to the performer and mouth 160 at upper end 140 is held open so as to present volume 146 bound by sleeve body 121 to receive a performer's foot of lower appendage 70. The lower appendage 70 is then foot first into volume 146 of garment 10 by introducing the performer's foot 71 to volume 146 through mouth 160 as thigh-receiving sleeve 150 is pulled upward in a longitudinal direction over the foot. Because sleeve body 121 is constructed of a material and in such a fashion as to resist stretching in the longitudinal direction, stretching in the longitudinal direction is limited to facilitate a user pulling garment 120 on so as to advance thigh-receiving sleeve 150 up performer's lower appendage 70 in response to performer's pulling in the longitudinal direction in a direction up the performer's leg. Garment 120 is so pulled and advanced over the lower appendage 70, which is, in turn, pushed into and through volume 146 of garment 120 as garment 120 is pulled on. The foot enters volume 146 through mouth 160 as performer continues to pull garment 120 upward in a longitudinal direction and push her foot into and through garment 102, and garment 120 so advanced over the performer's foot and past the user's ankle and onto leg 74. Because garment 120 is constructed of a material and in such a fashion as to allow elastic stretching radially, sleeve body 121 expands to accommodate the size of performer's foot. Indeed, because garment 120 is constructed of a material and in a fashion so as to allow elastic stretching radially in a direction that is perpendicular relative to the length of sleeve body 121 from upper end 140 to lower end 141, sleeve body 121 is capable of elastically expanding and contracting in the radial direction relative to the longitudinal direction of sleeve body 121 to accommodate many different sizes of feet. The foot continues to pass through volume 146 from upper end 140 to lower end 141 and outwardly through leg opening 163, and garment 120 is so advanced past performer's foot and ankle and onto leg 74 and then upwardly along leg 74 to knee 75, whereby lower thigh 76 of lower appendage 70 near knee 75 is received in, or otherwise applied to, thigh-receiving sleeve 150, the performer's knee 75 is received in, or otherwise applied to, knee-receiving sleeve 150, and upper leg 74 near knee 75 is received in, or otherwise applied to, leg-receiving sleeve 152, arranging garment 120 in the worn condition and ready for use. With front portion 130 facing forwardly relative to the performer during this installation procedure, front portion 130 formed with upper and lower gripping parts 180,181 are applied across and along the front or top of lower appendage 70 from knee 75 to and extending to upper leg 74 and lower thigh 76, knee pad 174 is applied to and covers the front of knee 75, and rear portion 131 is applied across and along the back of knee 75, whereby knee opening 170 is located so as to expose the back of knee 75, e.g., the popliteal fossa, of lower appendage 70. Although the process of moving garment 120 from a free condition to a worn condition on the knee region of lower appendage 70 as described is presented and described above as a series of sequential steps, it should be understood that the installation of garment 120 to lower appendage 70 is preferably accomplished in a single, continuous motion.

When so installed onto the knee 75 and the upper leg 74 and lower thigh 76 on either side of knee 75 of the lower appendage 70 of a human performer as described, front portion 130 is applied to and across the top or front side of the performer's lower thigh 75, upper leg 74, and knee 75, rear portion 131 is applied to and across the bottom or backside of the performer's lower thigh 76, upper leg 74, and knee 75, and side portions 132 and 133 are applied to and across the opposed sides, respectively, of the performer's lower thigh 76, knee 75, and upper leg 74. In this orientation of garment 120 when installed on a performer lower extremity 70 as described, upper gripping part 180 of thigh-receiving sleeve 150 of garment 120 is positioned near upper end 140 of sleeve body 121 on the performer's lower thigh 76 near knee 75 between the performer's knee 75 and upper thigh or hip and extends across or otherwise wraps about the rear or backside of the performer's lower thigh 76 near knee 75 between the performer's knee 75 and upper thigh or hip from near the top or front side of the performer's lower thigh 76 at one side of the performer's lower thigh 76 to near the top or front side of the performer's lower thigh 76 at the opposed side of the performer's lower thigh 76. Lower gripping part 181 of leg-receiving sleeve 152 of garment 120 is, in turn, positioned near lower end 141 of sleeve body 121 on the performer's upper leg 74 near knee 75 between the performer's knee 75 and lower leg or ankle and extends across or otherwise wraps about the rear or backside of the performer's upper leg 74 near knee 75 between the performer's knee 75 and lower leg or ankle from near the top or front side of the performer's upper leg 74 at one side of the performer's upper leg 74 to near the top or front side of the performer's upper leg 74 at the opposed side of the performer's upper leg 74.

And so lower appendage 70 is applied foot first into volume 146 through mouth 160 while garment 120 is held front portion 130 up or forward relative to the performer and garment 120 is pulled upwardly along lower appendage 70 over the performer's upper leg 74, knee 75, and lower thigh 76. In the worn condition, a portion of lower thigh 76 between the performer's knee 75 and upper thigh or hip is girdled by thigh-receiving sleeve 150, the performer's knee is girdled by knee-receiving sleeve 151, and a portion of upper thigh 74 between the performer's knee 75 and lower leg or ankle is girdled by leg-receiving sleeve 152. Front portion 130 of thigh-receiving sleeve 150 extends between knee-receiving sleeve 151 and upper end 140 of sleeve body 121 and is applied over and across the front of the lower thigh 76 girdled by thigh-receiving sleeve 150, and rear portion 131 of thigh-receiving sleeve 150 extends between knee-receiving sleeve 151 and upper end 140 of sleeve body 121 and is applied over and across the rear of the lower thigh 76 girdled by thigh-receiving sleeve 150. Front portion 130 of knee-receiving sleeve 151 extends between thigh-receiving sleeve 150 and leg-receiving sleeve 152 and is, together with knee pad 74, applied over and across the front of the knee 75 girdled by knee-receiving sleeve 151, and rear portion 131 of knee-receiving sleeve 151, including knee opening 170, extends between thigh-receiving sleeve 150 and leg-receiving sleeve 152 of sleeve body 121 and is applied over and across the rear of the knee 75 girdled by knee-receiving sleeve 151. Front portion 130 of leg-receiving sleeve 152 extends between knee-receiving sleeve 151 and lower end 141 of sleeve body 121 and is applied over and across the front of the upper leg 74 girdled by leg-receiving sleeve 152, and rear portion 131 of leg-receiving sleeve 152 extends between knee-receiving sleeve 151 and lower end 141 of sleeve body 121 and is applied over and across the rear of the upper leg 74 girdled by leg-receiving sleeve 152.

In this installation of garment 120, upper gripping part 180, circumferentially located upon and about outer surface 143 of thigh-receiving sleeve 150 of sleeve body 121 near upper end 140 and which extends across outer surface 143 of rear portion 131 of thigh-receiving sleeve 150 of sleeve body 121 from side portion 132 near front portion 130 to side portion 133 near front portion 130, girdles lower thigh 76 such that it circumferentially runs across the back of lower thigh 76 from side marginal edge 191 of upper gripping part 180 near side portion 132 near front portion 130 of thigh-receiving sleeve 150 of sleeve body 121 applied along the rear of lower thigh 76 along one side of lower thigh 76 to side marginal edge 192 of upper gripping part 180 near side portion 132 near rear portion 131 of thigh-receiving sleeve 150 of sleeve body 121 applied along the rear of lower thigh 76 along the opposed side of lower thigh 76. Lower gripping part 181, circumferentially located upon and about outer surface 143 of leg-receiving sleeve 152 of sleeve body 121 near lower end 141 and which extends across outer surface 143 of rear portion 131 of leg-receiving sleeve 152 of sleeve body 121 from side portion 132 near front portion 130 to side portion 133 near front portion 130, girdles leg 74 such that it circumferentially runs across the back of upper leg 74 from side marginal edge 191' of lower gripping part 181 near side portion 132 near front portion 130 of leg-receiving sleeve 152 of sleeve body 121 applied along the rear of upper leg 74 along one side of upper leg 74 to side marginal edge 192' of lower gripping part 181 near side portion 132 near rear portion 131 of leg-receiving sleeve 152 of sleeve body 121 applied along the rear of upper leg 74 along the opposed side of upper leg 74. With this installation of garment 120 with respect to lower appendage 70, upper and lower gripping parts 180,181 are applied to the backs of lower thigh 76 and upper leg 74 of the performer's lower appendage 70 such that upper and lower gripping parts 180,181 are positioned rearwardly along the back or rearward region of the performer's lower appendage 70 at the knee region of lower appendage 70 making such upper and lower gripping parts 180,181 available for gripping in a direction from the back or rear of the knee region of the performer's lower appendage 70, which is particularly useful for pole-dancing activities.

The elastically constrictive characteristic imparted by the material and construction of sleeve body 121, and the receipt of lower appendage 70 within volume 146, cooperate to hold garment 120 in place on performer's lower appendage 70 in the worn condition. Other conventional methods of application exist and should be apparent. To easily remove garment 120, one must merely pull lower end 141 of garment 120 in a direction opposite to that required to apply garment 120 to lower appendage 70. Alternatively, garment 120 is rolled downwardly upon itself from upper end 140 to lower end 141 and then pulled off foot the performer's foot. Other conventional methods of removal exist and should be apparent.

In the worn condition, garment 120 can be used for any desired purpose or action, but is particularly suitable in pole-dancing activity and training, in which garment 120 allows performer to train longer, more effectively, and with less risk of injury than would otherwise be possible, for reasons explained herein. Garment 120 provides overlying and protective resistance to performer's lower appendage 70 from bruising, burning, rubbing, and other effects caused by contact of performer's lower appendage 70 against a metal pole, and knee pad 74 provides padded protection knee 75 to allow a user to engage in prolonged kneeling or contact with an object, such as a pole-dancing pole. With garment 1s0 applied to performer's lower appendage 70 in the worn condition, contact areas 196 and 196' relate to "hot" points of the back of lower thigh 76 and upper leg 74 making garment 120 uniquely structured to assist performer in pole-dancing activity to allow performer to grip the pole along the back and sides of performer's lower appendage 70 at the knee region. In pole-dancing activities, contact areas 196 and 196' are placed against the pole and used as leverage points at which force or torque is applied from lower appendage 70 to the pole. The compressible radial thickness of sleeve body 121, and knee pad 74, provide cushioning, and sleeve body 121, together with upper gripping part 180 and lower gripping part 181 overlying sleeve body 121, protects lower appendage 70 at the knee region from bruising, burning, rubbing, and other effects caused by pole-dancing activities, allowing performer to train and resist fatigue and injury longer than compared to when no garment is worn. Moreover, knee opening 170 prevents binding of garment 120 at the back of knee 75 and promotes user comfort. Gaps 200 and 200' along front portion 130 of sleeve body 1s1 also provides a smooth, non-tacky surface extending from upper end 140 to lower end 141 of garment 120, providing performer a longitudinal area extending from upper end 140 to lower end 141 that does not grippingly engage a metal pole.

Although the assistive and protective garment 120 set forth in this disclosure is particularly useful in pole dance activities, garment 120 is equally usefully in assisting and protecting a user during other activities, such as sports activities, gymnastics and especially balance beam gymnastics activities, exercising activities, and the like, where a user may come into contact with sports, gymnastics, and exercising equipment or implements. The deformable, pliant, elastic, and elastically constrictive material characteristics of garment 120, and the deformable, pliant, and flexible material characteristics of gripping parts 180,181, permit garment 120, including gripping parts 180,181 to yield and deform in response to performer movement, and tends to hold garment 10 in place on the performer without restricting user movement.

The present invention is described above with reference to preferred embodiments. However, those skilled in the art will recognize that changes and modifications may be made in the described embodiments without departing from the nature and scope of the present invention. Various further changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

The invention claimed is:
1. A garment, consisting of:
a close-fitting sleeve body, formed of a stretch textile, has an open upper end, an open lower end, and a body-receiving volume extending through the sleeve body from the open upper end to the open lower end;
opposed, spaced-apart, surface-gripping parts are applied exteriorly to the sleeve body near the open upper end and the open lower end, respectively;
the surface-gripping parts are each formed of a gripping material different from the stretch textile, the gripping material is flexible, inelastic, and has an exposed outer surface that is slightly sticky or adhesive so as to together cause the exposed outer surface of each of the surface-gripping parts to grip, and to resist slipping relative to, surfaces they come in direct contact with without leaving a resulting residue on touched surfaces; and
the stretch textile resists lengthwise stretching in a longitudinal direction from the open upper end to the open lower end, and elastically stretches and constricts radially in a crosswise direction perpendicular to the longitudinal direction allowing the close-fitting sleeve body to elastically circumferentially expand and contract.

* * * * *